US009259585B2

(12) United States Patent
Vajha et al.

(10) Patent No.: US 9,259,585 B2
(45) Date of Patent: *Feb. 16, 2016

(54) FOLDED ANTENNAS FOR IMPLANTABLE MEDICAL DEVICES

(71) Applicant: Cardiac Pacemakers, Inc., St. Paul, MN (US)

(72) Inventors: Sasidhar Vajha, Maple Grove, MN (US); Keith R. Maile, New Brighton, MN (US); Dennis E. Larson, White Bear Township, MN (US); David A. Chizek, Brooklyn Park, MN (US); John M. Edgell, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/270,132

(22) Filed: May 5, 2014

(65) Prior Publication Data
US 2014/0243930 A1 Aug. 28, 2014

Related U.S. Application Data

(63) Continuation of application No. 13/302,282, filed on Nov. 22, 2011.

(60) Provisional application No. 61/416,655, filed on Nov. 23, 2010, provisional application No. 61/416,665, filed on Nov. 23, 2010, provisional application No. 61/416,663, filed on Nov. 23, 2010.

(51) Int. Cl.
*A61N 1/372* (2006.01)
*H01Q 1/36* (2006.01)
*H01Q 9/04* (2006.01)

(52) U.S. Cl.
CPC .............. *A61N 1/37229* (2013.01); *H01Q 1/36* (2013.01); *H01Q 9/0414* (2013.01); *Y10T 29/49016* (2015.01)

(58) Field of Classification Search
CPC ... A61N 1/37229; A61B 5/0015; H01Q 1/36; H01Q 1/362; H01Q 9/0414
USPC .............................. 607/36, 37, 57, 60; 604/19
See application file for complete search history.

(56) References Cited

U.S. PATENT DOCUMENTS

| 5,929,825 A | 7/1999 | Niu et al. |
| 6,456,256 B1 | 9/2002 | Amundson et al. |

(Continued)

FOREIGN PATENT DOCUMENTS

| CN | 103269750 A | 8/2013 |
| CN | 103298522 A | 9/2013 |

(Continued)

OTHER PUBLICATIONS

U.S. Appl. No. 13/302,202, Examiner Interview Summary mailed Dec. 10, 2013, 3 pgs.

(Continued)

*Primary Examiner* — Christopher D Koharski
*Assistant Examiner* — Jeremiah Kimball
(74) *Attorney, Agent, or Firm* — Schwegman Lundberg & Woessner, P.A.

(57) ABSTRACT

In an example, an apparatus can include an implantable medical device comprising a housing, an implantable telemetry circuit carried within the housing, a dielectric compartment mechanically coupled to the housing, the dielectric compartment including first and second substantially parallel face portions and a third face portion extending between the first and second face portions, and an implantable telemetry antenna, located at least partially within the dielectric compartment. The implantable telemetry circuit can be electrically coupled to the implantable telemetry antenna and configured to wirelessly transfer information electromagnetically using the implantable telemetry antenna. In an example the implantable telemetry antenna comprises a spiral conductor portion extending along the first, second, and third face portions. In an example the spiral conductor includes a cross section having a lateral width that can be greater than a sidewall height of the cross section.

18 Claims, 18 Drawing Sheets

(56) References Cited

U.S. PATENT DOCUMENTS

| | | | |
|---|---|---|---|
| 7,309,262 | B2 | 12/2007 | Zart et al. |
| 7,317,946 | B2 | 1/2008 | Twetan et al. |
| 7,532,932 | B2 | 5/2009 | Denker et al. |
| 7,917,226 | B2 | 3/2011 | Nghiem et al. |
| 8,170,680 | B2 | 5/2012 | Ameri |
| 8,195,305 | B2 | 6/2012 | Nghiem et al. |
| 8,761,896 | B2 * | 6/2014 | Vajha et al. ............... 607/60 |
| 2004/0082977 | A1 | 4/2004 | Engmark et al. |
| 2006/0247711 | A1 | 11/2006 | Verhoef et al. |
| 2008/0021522 | A1 | 1/2008 | Verhoef et al. |
| 2008/0303728 | A1 | 12/2008 | Lee et al. |
| 2009/0192574 | A1 | 7/2009 | Von Arx et al. |
| 2009/0228074 | A1 | 9/2009 | Edgell et al. |
| 2009/0228075 | A1 | 9/2009 | Dion |
| 2009/0228076 | A1 | 9/2009 | Ameri |
| 2010/0100157 | A1 | 4/2010 | Nghiem et al. |
| 2010/0168818 | A1 | 7/2010 | Barror et al. |
| 2011/0082523 | A1 | 4/2011 | Nghiem et al. |
| 2012/0130206 | A1 | 5/2012 | Vajha et al. |
| 2012/0130450 | A1 | 5/2012 | Vajha et al. |
| 2012/0130451 | A1 | 5/2012 | Vajha et al. |
| 2013/0009838 | A1 | 1/2013 | Nghiem et al. |
| 2013/0009839 | A1 | 1/2013 | Nghiem et al. |
| 2014/0364714 | A1 | 12/2014 | Ameri et al. |

FOREIGN PATENT DOCUMENTS

| | | | |
|---|---|---|---|
| CN | 103298523 | A | 9/2013 |
| JP | 9298417 | A | 11/1997 |
| JP | 2003505964 | A | 2/2003 |
| JP | 2007110539 | A | 4/2007 |
| JP | 2008537386 | A | 9/2008 |
| JP | 2013544598 | A | 12/2013 |
| JP | 2014504903 | A | 2/2014 |
| JP | 2014505501 | A | 3/2014 |
| WO | WO-02076289 | A2 | 10/2002 |
| WO | WO-2006104847 | A1 | 10/2006 |
| WO | WO-2008117898 | A1 | 10/2008 |
| WO | WO-2010045464 | A1 | 4/2010 |
| WO | WO-2010050852 | A1 | 5/2010 |
| WO | WO-2012/071402 | A1 | 5/2012 |
| WO | WO-2012071397 | A1 | 5/2012 |
| WO | WO-2012071410 | | 5/2012 |

OTHER PUBLICATIONS

U.S. Appl. No. 13/302,202, Final Office Action mailed Oct. 16, 2013, 13 pgs.

U.S. Appl. No. 13/302,202, Non Final Office Action mailed Jun. 26, 2013, 13 pgs.

U.S. Appl. No. 13/302,202, Notice of Allowance mailed Dec. 26, 2013, 11 pgs.

U.S. Appl. No. 13/302,202, Response filed Dec. 9, 2013 to Final Office Action mailed Oct. 16, 2013, 13 pgs.

U.S. Appl. No. 13/302,202, Response filed Sep. 26, 2013 to Non-Final Office Action mailed Jun. 26, 2013, 18 pgs.

U.S. Appl. No. 13/302,282, Non Final Office Action mailed Apr. 11, 2014, 8 pgs.

U.S. Appl. No. 13/302,282, Response filed Feb. 12, 2014 to Restriction Requirement mailed Jan. 16, 2014, 6 pgs.

U.S. Appl. No. 13/302,282, Restriction Requirement mailed Jan. 16, 2014, 7 pgs.

U.S. Appl. No. 13/302,324, Final Office Action mailed May 13, 2013, 7 pgs.

U.S. Appl. No. 13/302,324, Final Office Action mailed Dec. 23, 2013, 10 pgs.

U.S. Appl. No. 13/302,324, Non Final Office Action mailed Mar. 7, 2013, 7 pgs.

U.S. Appl. No. 13/302,324, Non Final Office Action mailed Aug. 12, 2013, 8 pgs.

U.S. Appl. No. 13/302,324, Response filed Apr. 17, 2013 to Non Final Office Action mailed Mar. 7, 2013, 14 pgs.

U.S. Appl. No. 13/302,324, Response filed Jul. 8, 2013 to Final Office Action mailed May 13, 2013, 14 pgs.

U.S. Appl. No. 13/302,324, Response filed Nov. 12, 2013 to Non Final Office Action mailed Aug. 12, 2013, 13 pgs.

Australian Application Serial No. [Pending], First Statement of Proposed Amendments filed May 20, 2013, 9 pgs.

International Application Serial No. PCT/US2001/061820, Written Opinion mailed Feb. 21, 2012, 5 pgs.

International Application Serial No. PCT/US2011/061820, International Preliminary Report on Patentability mailed Jun. 6, 2013, 7 pgs.

International Application Serial No. PCT/US2011/061820, International Search Report mailed Feb. 21, 2012, 3 pgs.

International Application Serial No. PCT/US2011/061829, International Preliminary Report on Patentability mailed Jun. 6, 2013, 8 pgs.

International Application Serial No. PCT/US2011/061829, International Search Report mailed Mar. 5, 2012, 4 pgs.

International Application Serial No. PCT/US2011/061829, Written Opinion mailed Mar. 5, 2012, 6 pgs.

International Application Serial No. PCT/US2011/061837, International Preliminary Report on Patentability mailed Jun. 6, 2013, 8 pgs.

International Serial Application No. PCT/US2011/061837, International Search Report mailed Feb. 23, 2012, 4 pgs.

International Serial Application No. PCT/US2011/061837, Written Opinion mailed Feb. 23, 2012, 6 pgs.

Abadia, Javier, et al., "3D-Spiral Small Antenna Deign and Realization for Biomedical Telemetry in the MICS band", Radioenginering, col. 18, No. 4, (Dec. 2009), 359-367.

Kwak, Sang Il, et al., "Ultra-wide band Spiral shaped small Antenna for the Biomedical Telemetry", APMC2005 Proceedings, (Dec. 2005). 4 pgs.

Rahmat-Samii, Yahya, et al., "Implanted Antennas in Medical Wireless Communications", Synthesis Lectures on Antennas (1), (2006), 82 pgs.

Soontornpipit, Pichitpong, et al., "Design of implantable microstrip antenna for communication with medical implants", IEEE Transactions on Microwave Theory and Techniques, 52(8), (2004), 1944-1951.

Sun, B., et al., "Compact monopole antenna for GSM/DCS operation of mobile handsets", Electronics Letters, 39(22), (Oct. 30, 2003), 1562-1563.

U.S. Appl. No. 13/302,202, Supplemental Notice of Allowability mailed May 23, 2014, 2 pgs.

U.S. Appl. No. 13/302,282, Advisory Action mailed Jan. 29, 2015, 3 pgs.

U.S. Appl. No. 13/302,282, Examiner Interview Summary mailed Jan. 29, 2015, 2 pgs.

U.S. Appl. No. 13/302,282, Final Office Action mailed Nov. 7, 2014, 9 pgs.

U.S. Appl. No. 13/302,282, Notice of Allowance mailed Apr. 10, 2015, 5 pgs.

U.S. Appl. No. 13/302,282, Response filed Jan. 7, 2015 to Final Office Action mailed Nov. 7, 2014, 11 pgs.

U.S. Appl. No. 13/302,282, Response filed Feb. 5, 2015 to Advisory Action mailed Jan. 29, 2015, 14 pgs.

U.S. Appl. No. 13/302,282, Response filed Jul. 8, 2012 to Non Final Office Action mailed Apr. 11, 2014, 13 pgs.

Chinese Application Serial No. 201180056261.X, Office Action mailed Jun. 20, 2014, With English Translation, 11 pgs.

Chinese Application Serial No. 201180056261.X, Office Action mailed Dec. 2, 2014, With English Translation, 7 pgs.

Chinese Application Serial No. 201180063364.9, Office Action mailed Jun. 5, 2014, With English Translation, 8 pgs.

Chinese Application Serial No. 2011800633988, Office Action mailed Feb. 27, 2015, With English Translation, 17 pgs.

Chinese Application Serial No. 2011800633988, Office Action mailed Jun. 9, 2015, With English Translation, 5 pgs.

Chinese Application Serial No. 2011800633988, Office Action mailed Jul. 22, 2014, With English Translation, 18 pgs.

European Application Serial No. 11790836.8, Examination Notification Art. 94(3) mailed Oct. 28, 2014, 4 pgs.

European Application Serial No. 11791179.2, Examination Notification Art. 94(3) mailed Feb. 9, 2015, 4 pgs.

European Application Serial No. 11791181.8, Examination Notification Art. 94(3) mailed Feb. 4, 2015, 4 pgs.

(56) References Cited

OTHER PUBLICATIONS

Japanese Application U.S. Appl. No. 2013-541015, Office Action mailed Apr. 1, 2014, With English Translation, 7 pgs.
Japanese Application Serial No. 2013-541018, Final Office Action mailed Feb. 3, 2015, With English Translation, 2 pgs.
Japanese Application U.S. Appl. No. 2013-541018, Office Action mailed Jun. 24, 2014, With English Translation, 10 pgs.
Japanese Application Serial No. 2013-541021, Office Action mailed Jul. 1, 2014, With English Translation, 11 pgs.
Abadia, Javier, et al., "3D-Spiral Small Antenna Design and Realization for Biomedical Telemetry in the MICS band", Radioengineering vol. 18, No. 4, (Dec. 2009), 359-367.
Kwak, Sang Il, et al., "Ultra-wide band Spiral shaped small Antenna for the Biomedical Telemetry", APMC 2005 Proceedings, (2005), 4 pgs.
Soontornpipit, P., et al., "Design of implantable microstrip antenna for communication with medical implants", IEEE Transactions on Microwave Theory and Techniques, 52(8), (Aug. 2004), 1944-1951.
US 8,731,681, 05/2014, Vajha et al. (withdrawn)

* cited by examiner

FOLDED ANTENNAS FOR IMPLANTABLE MEDICAL DEVICES

CROSS REFERENCE TO RELATED APPLICATIONS

This application is a continuation of U.S. patent application Ser. No. 13/302,202, entitled "Folded Antennas for Implantable Medical Devices," filed on Nov. 22, 2011, now issued as U.S. Pat. No. 8,761,896, which is hereby incorporated by reference herein in its entirety.

This application claims benefit of priority under 35 U.S.C. 119(e) to:
1. Vajha et al., U.S. Provisional Patent Application Ser. No. 61/416,655, entitled "Folded Antennas for Implantable Medical Devices", filed on Nov. 23, 2010, which is hereby incorporated herein by reference in its entirety;
2. Vajha et al., U.S. Provisional Patent Application Ser. No. 61/416,665, entitled "Folded Antennas for Implantable Medical Devices", filed on Nov. 23, 2010, which is hereby incorporated herein by reference in its entirety; and
3. Vajha et al., U.S. Provisional Patent Application Ser. No. 61/416,663 entitled "Modular Antenna for Implantable Medical Device", filed on Nov. 23, 2010, which is hereby incorporated herein by reference in its entirety.

BACKGROUND

Implantable medical devices (IMDs) can perform a variety of diagnostic or therapeutic functions. In an example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), cardiac resynchronization therapy (CRT) devices, implantable monitors, neuromodulation devices (e.g., deep brain stimulators, or other neural stimulators), cochlear implants, or drug pumps, among other examples.

Such IMDs can include electronic circuitry configured to wirelessly transfer information between implanted IMDs, or between an IMD and an assembly external to the body. Such information can include, for example, programming instructions or configuration information to configure the IMD to monitor, diagnose, or treat a physiologic condition. Such information can also include data sensed, detected, or processed by the IMD and transmitted to another device or assembly (e.g., physiologic information, a disease status, etc.) An IMD can include an antenna sized and shaped to wirelessly transfer information, such as using a desired operating frequency range. Such a frequency range can be specified by a spectrum allocation authority within the country where the IMD may be located or used. Thus, the IMD generally includes an antenna tailored to the spectrum allocation regulations where the IMD may be used or sold.

OVERVIEW

Generally, active implantable medical devices (IMDs) can include a pacemaker, a defibrillator, a cardiac resynchronization therapy device, a neurostimulation device, an implantable monitoring device, or one or more other devices. Information can be wirelessly transmitted to, or received from, such IMDs, such as using electromagnetic waves. Such electromagnetic waves can be transmitted or received using an implantable antenna included as a portion of the IMD. Such electromagnetic transmission can provide an effective communication range on the order of meters, as compared using a communication scheme involving mutual-inductive magnetic coupling. Such magnetic coupling is generally limited to an effective communication range of only centimeters.

In Zart et al. (U.S. Pat. No. 7,309,262), a connector assembly for an implantable medical device is mentioned. The connector assembly includes a core element formed of a thermoplastic material, and a circuit member including an antenna structure extending over a portion of the core element outer surface.

In Abadia et al., "3D-Spiral Small Antenna Design and Realization for Biomedical Telemetry in the MICS band," Radioengineering, vol. 18, no. 4, (December 2009), pp. 359-367, a dielectric-loaded antenna including a coaxial feed, a ground plane, and a grounding pin between a metal patch portion of the antenna and the ground plane are provided.

In Kwak, "Ultra-wide band Spiral shaped small Antenna for the Biomedical Telemetry," APMC2005 Proceedings, Institute for Electrical and Electronics Engineers (2005), a coaxially-fed spiral antenna for biomedical telemetry is mentioned. The antenna includes a flat conductor on a dielectric material, above a ground plane, in an air-filled capsule.

After an IMD is implanted, it is generally surrounded by various bodily tissues or fluids. Such tissues or fluids (e.g., muscle tissue, fatty tissue, bone, blood, etc.) are somewhat conductive (e.g., lossy), inhomogeneous (e.g., having a varying loss and dielectric permittivity), and can have a relatively high dielectric permittivity as compared to free space. Because the medium surrounding the IMD in vivo can vary, and is different than a free space environment, the implantable antenna included as a portion of the IMD can be located at least partially within a dielectric compartment. Such a dielectric compartment can protect the implantable antenna from exposure to tissue or bodily fluids that may degrade antenna performance. Also, the dielectric compartment can improve operating consistency of the implantable antenna (e.g., a usable range, a directivity, a gain, or other performance) for both a free-space use environment before implant, and an in vivo environment after implant.

The present inventors have recognized, among other things, that the total volume of space occupied by an IMD can be an important consideration to both implanting physicians and patients. Thus, the size and shape of a dielectric compartment including the implantable antenna can be determined in part by spatial constraints (e.g., an allowable volume or surface area), and by biocompatibility considerations (e.g., a material or a shape can be selected to be compatible with, and unobtrusive to, the patient), rather than just electrical performance considerations. However, antenna length and volume are still generally governed by electrical performance needs as well. Generally, an antenna length, such as for a monopole antenna, can be about an odd-multiple of a quarter of a wavelength in a specified medium (e.g., ¼ of a wavelength, ¾ of a wavelength, etc.), corresponding to a desired resonant operating frequency within a desired operating frequency range.

As the desired operating frequency range decreases in frequency, the length and volume occupied by a relatively straight quarter-wavelength monopole (or half-wavelength dipole antenna) can become undesirably large, despite the higher relative dielectric permittivity of a tissue environment. For example, in some countries, wireless transfer of information can use a first specified range of frequencies around 900 megahertz (MHz), or some other range of frequencies, such as specified by a spectrum allocation authority. However, in other countries, or at the preference of a health care provider or caregiver, a second specified range of frequencies around 400 MHz may be used instead of, or in addition to, the first specified range of frequencies. The present inventors have recognized, among other things, that the total length of an antenna designed to work at around 900 MHz may need to more than double in order for such an antenna to be used at around 400 MHz. Such a doubling in length may be unacceptable to end users because such a doubling in length may unacceptably increase the volume or area used by the implantable antenna.

Accordingly, the present inventors have also recognized that the implantable antenna can be made more compact than a straight monopole or straight dipole antenna, such as by using a more complex antenna shape, while still meeting design goals that constrain a total antenna volume or area. Moreover, the present inventors have also recognized that such a compact antenna, such as including one or more of a spiral conductor (e.g., a conductive material arranged in a spiral pattern), or another shape (e.g., a serpentine conductor shape), can still have a physical path length approaching a quarter wavelength (or a half wavelength in the case of a dipole antenna). In an example, an implantable antenna including a spiral conductor can provide electrical performance comparable to a straight monopole (or dipole) conductor.

In an example, such a spiral conductor or other shape, such as a serpentine conductor shape, can be fabricated in a substantially planar pattern (e.g., etched, stamped, or cut out of a sheet of material in a relatively flattened pattern, such as providing a conductive pattern having a ribbon-shaped conductor cross section). Then, such a planar pattern can be formed or folded into a configuration to conform to, or extend along, one or more faces of the dielectric compartment. In an example, such a dielectric compartment can include a header attached to an IMD, the header including one or more connectors to electrically or mechanically mate with one or more implantable leads.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
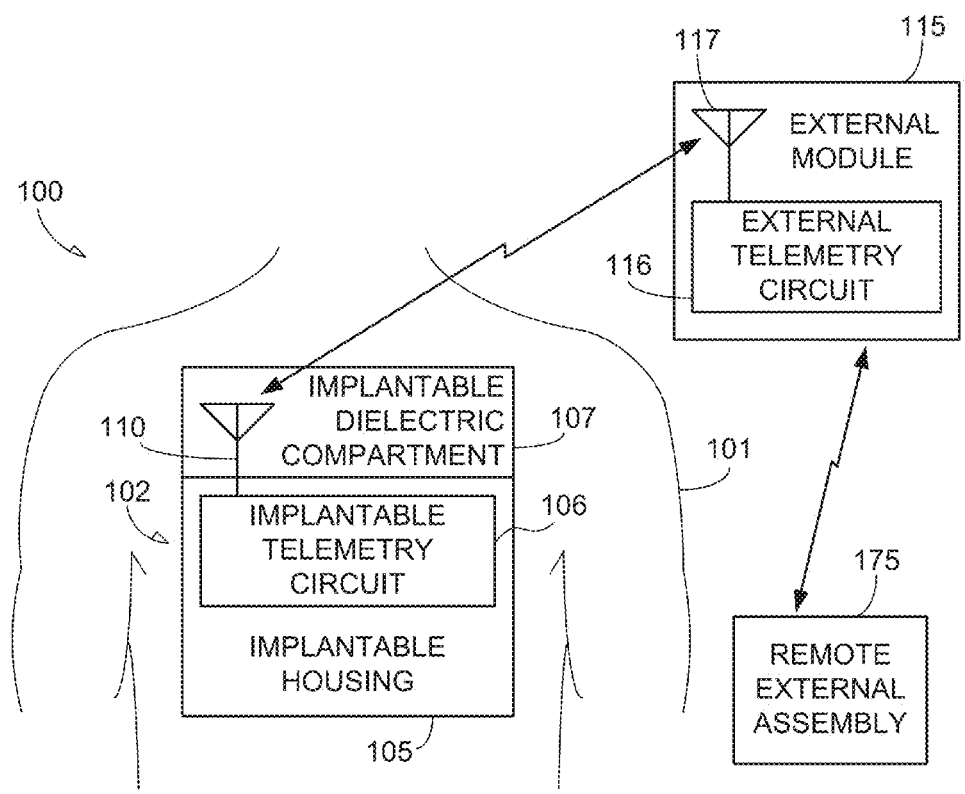
FIG. 1 illustrates generally an example of an apparatus that can include an implantable medical device wirelessly coupled to an external module.

FIG. 1 illustrates generally an example of an apparatus 100 that can include an implantable medical device (IMD) 102, implanted within a body (e.g., a patient 101), such as wirelessly coupled to an external module 115. In an example, the IMD 102 can include an implantable device housing 105, such as including a conductive portion (e.g., a hermetically-sealed titanium housing, or a housing including one or more other materials). For example, the housing 105 can contain at least a portion of an implantable telemetry circuit 106, such as a transmitter, a receiver, or a transceiver, configured to wirelessly transfer information electromagnetically using an implantable antenna 110 such as included at least partially within a dielectric compartment 107. In an example, the external module 115 can include an external antenna 117 coupled to an external telemetry circuit 116.

In an example, the external module can include a physician programmer, a bedside monitor, or other relatively nearby assembly, such as used to transfer programming instructions or configuration information to the IMD 102, or the receive diagnostic information, a disease status, information about one or more physiologic parameters, or the like, from the IMD 102. The external module 115 can be communicatively connected to one or more other external assemblies, such as a remote external assembly 175, located elsewhere (e.g., a server, a client terminal such as a web-connected personal computer, a cellular base-station, or another wirelessly-coupled or wired remote assembly). The implantable antenna 110 can include a spiral conductor, or one or more other conductor shapes or configurations, such as shown and discussed in the examples below.

Figure 2:
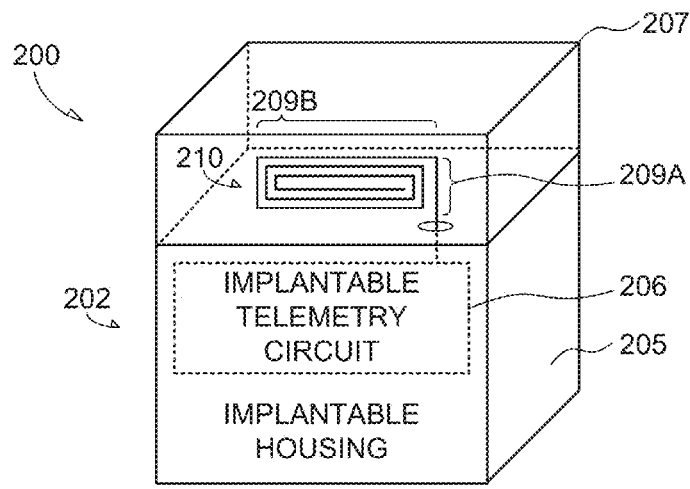
FIG. 2 illustrates generally an example of an apparatus that can include an implantable medical device, such as including an implantable telemetry circuit coupled to an implantable antenna including a spiral conductor.

FIG. 2 illustrates generally an example of an apparatus 200 that can include an IMD 202, such as including an implantable telemetry circuit 206 coupled to an implantable antenna 210 including a spiral conductor 209B. In the example of FIG. 2, the spiral conductor 209B can be fed by a conductive segment 209A. The conductive segment 209A can be substantially perpendicular to a surface or face of a housing 205, such as the housing 205 that comprises a conductive portion. For example, the conductive segment 209A can include a loading portion configured to adjust an input impedance of the implantable antenna 210, to provide an input impedance within a specified input impedance range at a specified range of frequencies. In an example, the conductive segment 209A can be used to reduce or eliminate a capacitive contribution to the input impedance of the implantable antenna 210, such as by reducing a capacitive interaction between the conductive segment 209A and the housing 205.

In an example, at least a portion of the implantable antenna 210 can be located at least partially on or within a dielectric compartment 207. For example, the dielectric compartment can include a biocompatible material such as an epoxy, a thermoplastic polyurethane (e.g., TECOTHANE™), or one or more other materials. In an example, the dielectric compartment can comprise a header including one or more connectors configured to mate with an implantable lead assembly, such as shown in the examples of FIG. 8-9, 10A-B, 11-18, 19A-B, 20A-B, or 21A-B. In an example, one or more of the spiral conductor 209B or the conductive segment 209A can include a ribbon shape or other cross section, such as shown in the examples of FIG. 8-9, 10A-B, 11-18, 19A-B, 20A-B, or 21A-B. In an example, the spiral conductor 209B can instead be replaced by one or more other conductive shapes, such as the serpentine conductor of FIG. 3B.

Figure 3A:
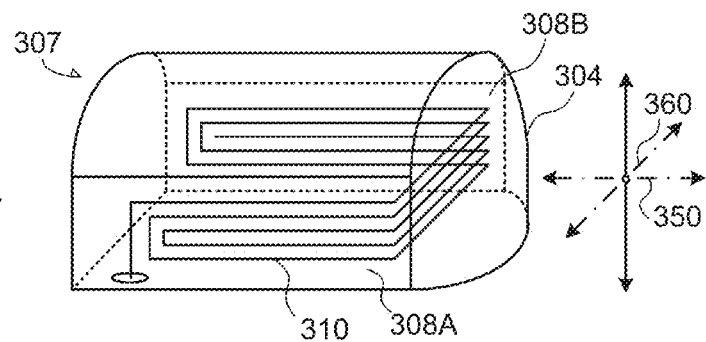
FIGS. 3A-B illustrate generally examples of an apparatus that can include an implantable antenna located at least partially within a dielectric compartment.
Figure 3B:
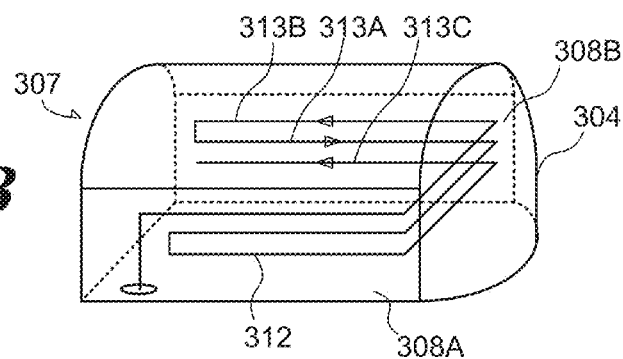

FIGS. 3A-B illustrate generally examples of an apparatus, such as a portion of the apparatus of the examples of FIGS. 1-2, that can include an implantable antenna located at least partially within a dielectric compartment 307. FIG. 3A depicts a hypothetical longitudinal axis 350 and an axis 360 perpendicular to the longitudinal axis 350. In the example of FIG. 3A, an antenna 310 including a spiral conductor can be located at least partially within the dielectric compartment 307 (e.g., a header, or another portion of an IMD, such as discussed in the examples above or below). In the example of FIG. 3A, the spiral conductor 310 can be oriented to extend along a first face 308A, a second face 308B, or a third face 304, of the dielectric compartment 307. For example, the first and second faces 308A-B can be substantially parallel (e.g., the sidewalls of the dielectric compartment 307). In an example, a third face 304 can extend between the first and second faces 308A-B, such as shown in FIG. 3A. In an example, the various faces of the dielectric compartment 307 need not be perfectly planar. In an example, the dielectric compartment 307 can be formed by one or more molding steps, such as using a thermosetting or a thermoplastic dielectric material.

In an example, unlike a helical or conical antenna, the spiral conductor 310 can include multiple "turns" in a plane perpendicular to a hypothetical axis. For example, for a portion of the spiral conductor 310 extending along the first face 308A, the turns of the spiral conductor can be "wound" concentrically in a plane substantially parallel to the first face 308A, along a hypothetical longitudinal axis 350. In an example, such as in FIG. 3A, each "turn" need not be circular. For example, for a portion of the spiral conductor 310 extending along the second face 308B, the turns can be again "wound" in a plane substantially parallel to the second face 308B, along the hypothetical longitudinal axis 350. In the example of FIG. 3A (and as similarly shown in the examples of FIGS. 7A-D), the planar spiral pattern can be folded to extend along more than one face of the dielectric compartment 307, such as to place the implantable antenna 310 at a specified depth from one or more of the first or second faces 308A-B, or the third face 304.

In the example of FIG. 3B, a serpentine antenna 312 can be similarly located on or within the dielectric compartment 307, such as including a first segment 313A extending along the first face, 308A, the second face 308B, and the third face 304. In the example of FIG. 3B, unlike the spiral conductor example of FIG. 3A, the instantaneous direction of a current flowing through the serpentine antenna 312, such as at or near resonance, can include a first direction (e.g., indicated by an arrow in FIG. 3B) associated with the first segment 313A. In such an example, the instantaneous current flowing through a second segment 313B, or a third segment 313C, can include a second, opposite, direction. In the example of FIG. 3B, the second and third segments 313B-C can extend along the lateral edges of the first segment 313A. However, if the first-third segments 313A-C are about the same depth from an exterior face of the dielectric compartment 307, the net radiated electromagnetic field is reduced as compared to the example of FIG. 3A. The decrease in the net radiated field can be due in part to a cancellation effect from the first and second current directions. For example, the electromagnetic field generated by the current flowing in the first direction is counteracted by the respective field contributions from the adjacent segments having respective currents flowing in the second, opposite, direction.

The present inventors have also recognized that this cancellation effect can be reduced somewhat by staggering the depths of the various segments with respect to an exterior face of the dielectric compartment 307. For example, in FIG. 3B, the first-third segments 313A-C are relatively uniform in spacing from the first and second faces 308A-B. In an example, the third segment 313 could be relatively further recessed within the dielectric compartment 307, as compared to the first and second segments 313A-B. Similarly, the first segment 313A could be recessed further into the dielectric compartment than the second segment 313B, but not quite as far recessed as the third segment 313C. In an example, staggering the depths of the first, second and third segments 313A-C can also reduce unwanted coupling between adjacent segments (e.g., due to a fringing field effect). Such unwanted coupling can generally increases the capacitive portion of the input impedance of the antenna, and can at least partially "short out" the current flowing on the antenna, reducing the antenna's effective length or radiation efficiency, for example.

Figure 4A:
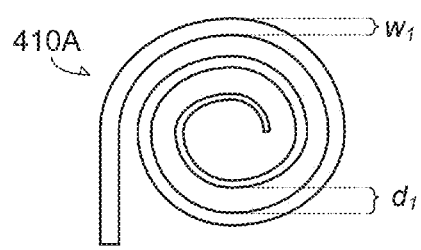
FIGS. 4A-B illustrate generally examples of an apparatus, such as a portion of the apparatus of the examples of FIGS. 1-2, that can include a spiral conductor having a specified shape or configuration.
Figure 4B:
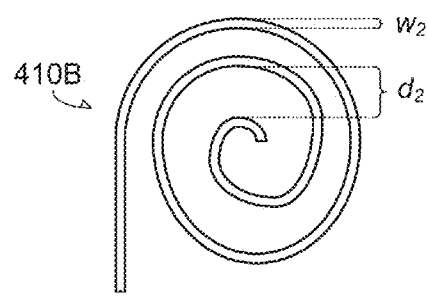

FIGS. 4A-B illustrate generally examples of an apparatus, such as a portion of the apparatus of the examples of FIGS. 1-2, that can include a spiral conductor 410A-B having a specified shape or configuration. In the example of FIG. 4A, a spiral conductor (e.g., similar to the spiral conductors included as a portion of the antenna 110, 210, or 310 shown in the examples of FIGS. 1-2, 3A) can include a specified distance between adjacent turns, "$d_1$." The spiral conductor 410A can also include a conductor having a specified lateral width, "$w_1$." In the example of FIG. 4A, the distance, "$d_1$," can be relatively uniform (e.g., constant) along the path of the spiral conductor 410A. In FIG. 4A, the lateral width, "$w_1$," can taper (or otherwise vary in a specified or controlled manner) along the path of the spiral conductor 410A.

Similarly, FIG. 4B illustrates an example where a lateral width, "$w_2$," can taper (or otherwise vary in specified or controlled manner), along the path of the spiral conductor 410B, while a distance, "$d_2$," between adjacent turns of the spiral conductor 410B can be relatively uniform. Such a tapering in either lateral width, or separation distance, or both, can be used at least in part to adjust or provide one or more desired electrical performance characteristics of an antenna including the spiral conductor 410A. For example, such adjustment can be used to provide a specified input impedance, a specified antenna gain, a specified directivity, or a specified current distribution along the antenna, or the like.

Figure 5A:
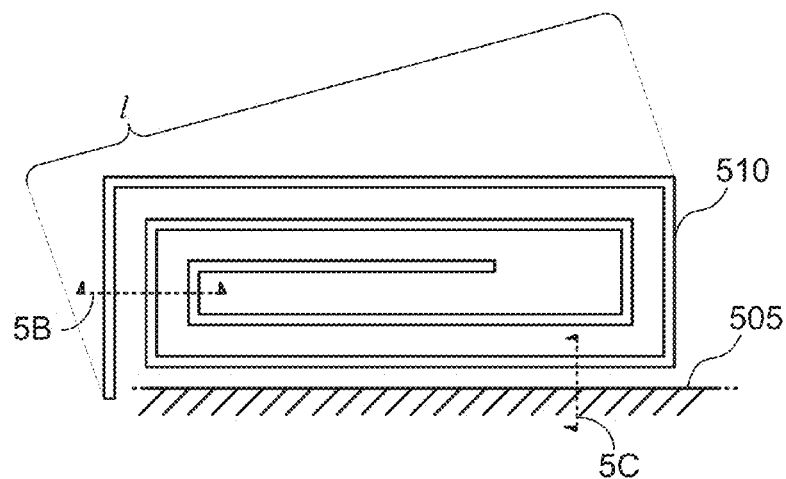
FIGS. 5A-C illustrate generally views of an example of at least a portion of an implantable antenna including a spiral conductor including a cross section having a lateral width that is greater than a sidewall height of the cross section, and having a specified separation between adjacent turns of the spiral conductor, and between the spiral conductor and another conductor.
Figure 5B:
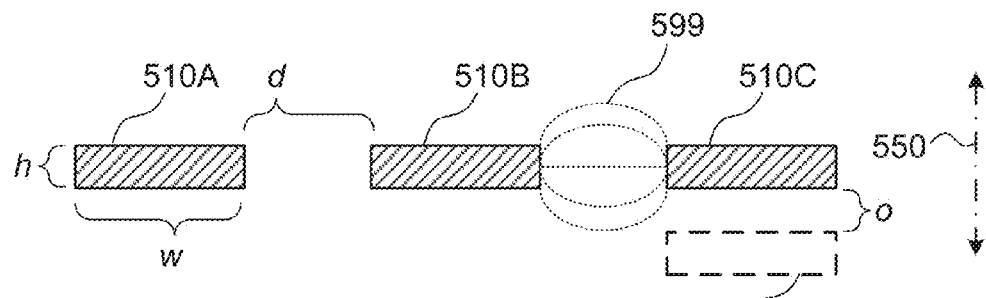
Figure 5C:
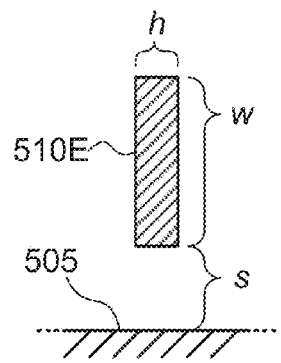

FIGS. 5A-C illustrate generally views of an example of at least a portion of an implantable antenna 510 including a spiral conductor. In the example of FIG. 5A, the antenna 510 can be monopole-like, such as using a conductive region 505 as a counterpoise (e.g., a reflector). In an example, an implantable antenna can include a dipole antenna (or another antenna type), such as using two (or more) similar spiral conductors each similar to the antenna 510 shown in FIGS. 5A-C. In such a dipole example, a counterpoise such as the conductive region 505 need not be included. The line labeled "5B" of FIG. 5A indicates a horizontal cross-section of antenna 510 that is shown in detail in FIG. 5B. The line labeled "5C" of FIG. 5A indicates a vertical cross-section of antenna 510 that is shown in detail in FIG. 5C.

The antenna 510 can include a cross section having a lateral width, "w," such as shown in FIG. 5B with respect to a first segment 510A in a first turn of the spiral conductor. In the examples of FIGS. 5A-C, the lateral width, "w," can be greater than a sidewall height, "h," of the cross section, again shown with respect to the first segment 510A in FIG. 5B. A specified separation, "d," can be used between adjacent turns of the spiral conductor, such as shown in FIG. 5B, between the first segment 510A in the first turn, and a second segment 510B in a second turn of the spiral conductor.

The present inventors have recognized, among other things, that various undesired effects such as current cancelation or fringing-field effects can be reduced or eliminated using various techniques. Such techniques can allow the spacing, "d," to be reduced as compared to antennas lacking such features as shown in FIGS. 5A-C. Such a reduction in spacing, "d," can provide an antenna 510 that is more compact (e.g., volumetrically, or in surface area) than antennas lacking such features as shown in FIGS. 5A-C. For example, use of a spiral conductor geometry as shown in FIGS. 5A-C can reduce current cancelation versus using the serpentine geometry of FIG. 3B, because the instantaneous currents in adjacent segments (e.g., segments 510A-C) generally flow in the same direction when the antenna is operating in a first resonant mode.

Another technique can include staggering adjacent segments or turns of the antenna 510 in depth, such as locating a third segment 510C in the region 510D, such as to reduce an interaction between adjacent segments due to a fringing field 599 (e.g., an electric field indicative of capacitive coupling between adjacent segments). While such a modification to the location of segment 510C can result in an antenna 510 that is not perfectly planar, such an antenna is still substantially planar, since the change in the position of the segment 510C to the location of the region 510D can be very small, such as represented by "o," in comparison to the total surface area of the plane of the antenna 510. For example, FIG. 5A can represent a view of a plane along a hypothetical axis 550 on which the antenna 510 is "wound." The dimension, "o," can represent an offset in depth between adjacent "turns" of the antenna, along the hypothetical axis 550. In an example, the total depth of the antenna 510 along such a hypothetical axis 550 can be at least an order of magnitude smaller than a diameter or a largest linear dimension, "l," of the antenna 510.

Yet another technique can include using an antenna 510 including ribbon-shaped cross section, such as a rectangular cross section as shown in FIGS. 5A-C, or an otherwise non-circular cross section, instead of using a wire or round cross section. The present inventors have recognized, among other things, that the antenna 510 including spiral conductor using a ribbon cross section, as shown in FIGS. 5A-C, can be made more compact than a corresponding helical antenna or wire antenna. For example, the fringing field 599 interaction between adjacent segments can be reduced if the ribbon conductor is oriented so that the thinner sidewalls are adjacent to one another as compared to locating the "fat" lateral portions of width "w" facing one another.

The illustrative examples of FIGS. 9, 10A-B, 11-18, 19A-B, 20A-B, and 21A-B generally show the interaction between various physical parameters such as including the dimensions "w," "h," "d," and "s." In an illustrative example, if the antenna 510 is to be used for wireless transfer of information electromagnetically at a specified range of frequencies around 400 MHz, then the width, "w," can be from a range of about 34 mils (0.034 inches) to about 50 mils (0.050 inches), or some other width. Generally, the sidewall height, "h," can be kept small for the reasons discussed above, but the thickness should not be so small that surface roughness increases resistance undesirably. In an illustrative example, a ribbon thickness (e.g., sidewall height, "h") can be larger than a "skin depth" of current at the desired operating frequency. At around 400 MHz, the skin depth is around 1 mil (0.001 inches). Thus, in such an illustrative example at 400 MHz, a surface roughness of about 0.1 mil (0.0001 inches) or less can be specified.

In an illustrative example, the distance between adjacent turns of the spiral conductor, "d," can be from about 15 mils (0.015 inches) to about 20 mils (0.020 inches), or some other distance, such as for providing consistent performance at a specified range of frequencies around 400 MHz, in both free space (e.g., air) or in a variety of different tissue media. Though the antenna 510 can be made more compact using a closer spacing of adjacent turns, such a closer spacing can result in a higher quality factor, "Q," corresponding to a reduced usable bandwidth as compared to an antenna having a wider spacing between adjacent turns.

In the example of FIG. 5C, the antenna 510 can be oriented so that the short sidewall of the spiral conductor is substantially parallel to the nearby conductive region 505. The conductive region 505 can be at "ground" potential for alternating current signals, thus a separation, "s," between a segment 510E and the conductive region 505 can be maintained, such as to avoid unwanted loading of the antenna 510 by the conductive region. Similar to the discussion above with respect to adjacent segments, orienting the segment 510E so that the short sidewall is adjacent to the conductive region 505 can allow a smaller separation, "s," than if the antenna had a round (e.g., wire) cross section, or if the antenna segment 510E were rotated 90 degrees so that the wider portion were closest to the conductive region 505. Thus, an antenna 510 can be "tucked" into a physically constrained area within a dielectric compartment, such as at the rear portion of a header for an IMD, while still maintaining a specified offset distance between the antenna 510 and adjacent conductive structures, such as a conductive housing of the IMD.

Figure 6A:
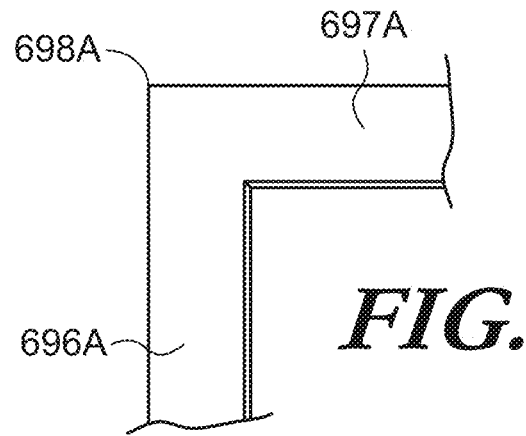
FIGS. 6A-C illustrate generally views of an example of at least a portion of an implantable antenna, such as shown in the examples of FIG. 1-2, 3A, 4A-B or 5A-C, such as including a first conductive segment and a second conductive segment mechanically and electrically coupled using a specified transition portion.
Figure 6B:
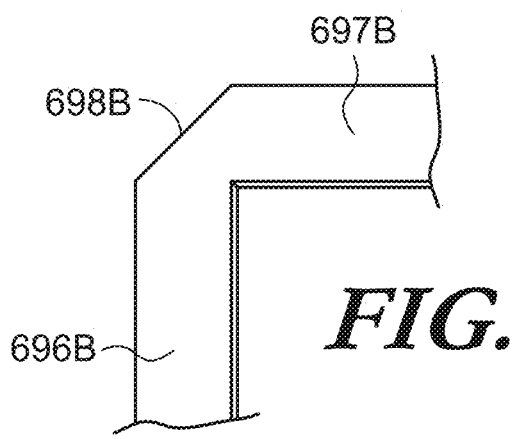
Figure 6C:
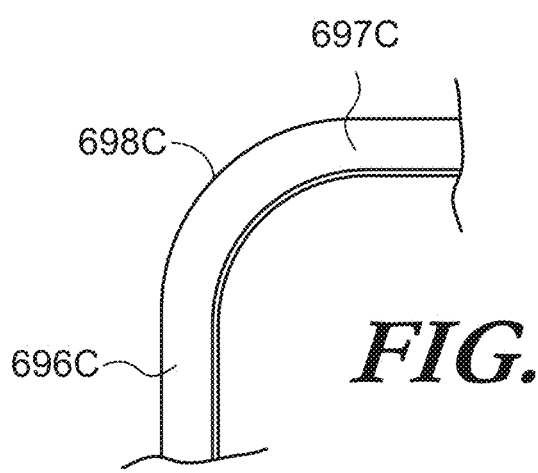

FIGS. 6A-C illustrate generally views of an example of at least a portion of an implantable antenna, such as shown in the examples of FIG. 1-2, 3A-B, 4A-B or 5A-C, such as including a first conductive segment and a second conductive segment mechanically and electrically coupled using a specified transition portion.

The examples of FIGS. 1-2, 3A, and 4A-B illustrate generally that an antenna for an IMD can include a spiral conductor. However, the spiral conductor need not include bends, radii, or transition portions for each turn that are the same for every turn, or for every junction between adjacent segments within a respective turn. In the example of FIG. 6A, a first segment 696A, such as ribbon-shaped conductor, can transition into a second segment 697A, such as using a 90-degree corner 698A. In the example of FIG. 6B, a first segment 696B can transition into a second segment 697B, such as via a "clipped" corner 698B. In the example of FIG. 6C, a first segment 696C can transition into a second segment 697C, such as using a radiused transition 698C. In an example, as operating frequency increases (e.g., an operating wavelength becomes shorter), power bundling or a concentration in current can occur if a sharp corner 698A or a clipped corner 698B is included, such as shown respectively in FIGS. 6A-B. For example, to avoid an unwanted peak in current magnitude, such as in a first or outer-most turn of an implantable antenna including a spiral conductor, the radiused transition of FIG. 6C can be used. Conversely, in an example, to provide a higher current density for one or more interior turns toward the center of the spiral conductor pattern, a sharper transition can be used, such as shown in the examples of FIG. 19A-B, 20A-B, or 21A-B. Such heightened current density on one or more interior turns can enhance radiation efficiency, while avoiding such sharp or clipped corners 698A-B on outer turns can help prevent an unwanted increase in a resistive contribution to an input impedance of the antenna.

Figure 7A:
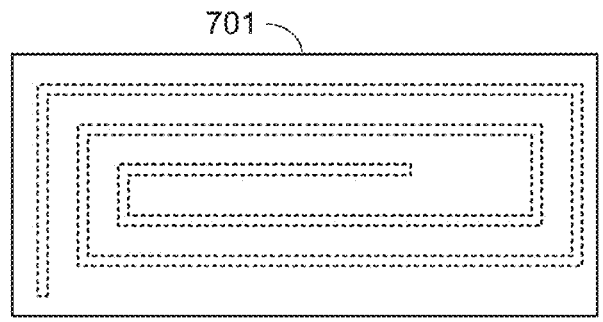
FIGS. 7A-D illustrate generally a technique for fabricating a spiral conductor, such as shown in the examples of FIG. 1-2, 3A, 4A-B or 5A-C, such as including patterning or etching a planar conductor to provide a planar spiral pattern, and folding or forming the planar spiral pattern into a specified configuration.
Figure 7B:
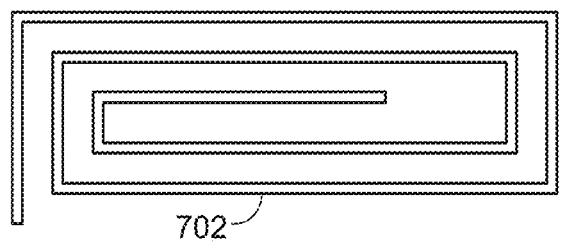

FIGS. 7A-D illustrate generally a technique for fabricating a spiral conductor, such as shown in the examples of FIG. 1-2, 3A, 4A-B or 5A-C, such as including patterning or etching a planar conductor to provide a planar spiral pattern, and folding or forming the planar spiral pattern into a specified configuration. In FIG. 7A, a sheet of conductive material 701 can be provided (e.g., a sheet of metal stock, etc.). Such material 701 can include one or more of aluminum, steel, stainless steel, a biocompatible alloy (e.g., platinum-iridium or another material), or a shape-memory material (e.g., a nickel-titanium alloy or other material). In an example, one or more portions of an implantable antenna can be patterned, etched, cut, stamped, or otherwise formed from the sheet of conductive material 701, such as to provide a substantially planar spiral conductor 702 as shown in FIG. 7B. In an example, such a conductor 702 can have a ribbon-shaped cross section, such as including a lateral width of a segment determined by the shape of the pattern, and including a sidewall height of the segment determined by the thickness of the sheet of stock 701.

In an example, the material 701 can be a conductive material cladding a dielectric material. For example, the material 701 can include one or more of copper, aluminum, gold, platinum, or one or more metals or alloys, such as cladding a flexible or rigid dielectric substrate. In an example, the dielectric substrate can include one or more of a polyimide, polytetrafluoroethylene (PTFE), expanded PTFE (ePTFE), polyether-ether-ketone (PEEK), a thermoplastic polyurethane, an epoxy, a glass-epoxy laminate, or one or more other flexible or rigid materials. In such a cladded example, the material 701 can be etched or patterned to provide a desired conductor geometry, similar to the conductor 702, such as fabricated using one or more processes or techniques generally used for printed circuit board (PCB) or printed wiring board (PWB) manufacturing.

Figure 7C:
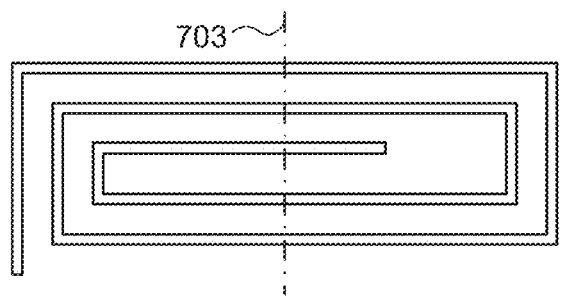
Figure 7D:
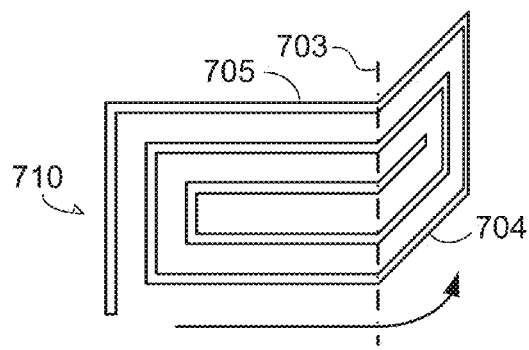

In an example, the conductor 702 can then be folded, bent, or otherwise formed into a desired two- or three-dimensional configuration, such as folded around a hypothetical axis 703, as shown in FIG. 7C, to provide an implantable antenna 710 having a specified configuration. In the example of FIG. 7D, the implantable antenna 710 can include a first substantially planar portion 705, and a second substantially planar portion 704. One or more of the first or second portions 704-705 can be overmolded, attached, inserted, or otherwise coupled to a dielectric material (e.g., a dielectric compartment included as a portion of an IMD), such that one or more of the first or second portions 704-705 extends along or is substantially parallel to a face of the dielectric material. In an example, the conductor 702 can be folded along more than one axis, such as shown in the example of FIG. 8, and elsewhere. In an example, one or more techniques similar to those shown in the examples of FIGS. 7A-D can be used, but instead including a serpentine antenna conductor pattern, such as shown in the example of FIG. 3B.

Figure 8A:
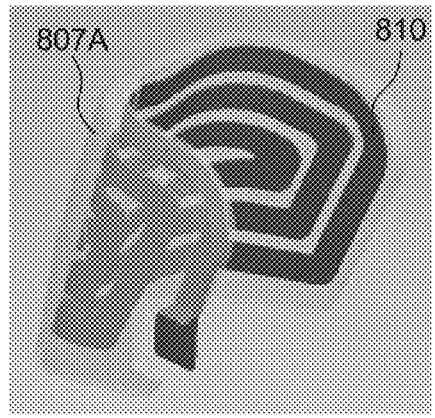
FIGS. 8A-C illustrate generally an example of an apparatus that can include a modular implantable antenna assembly.
Figure 8B:
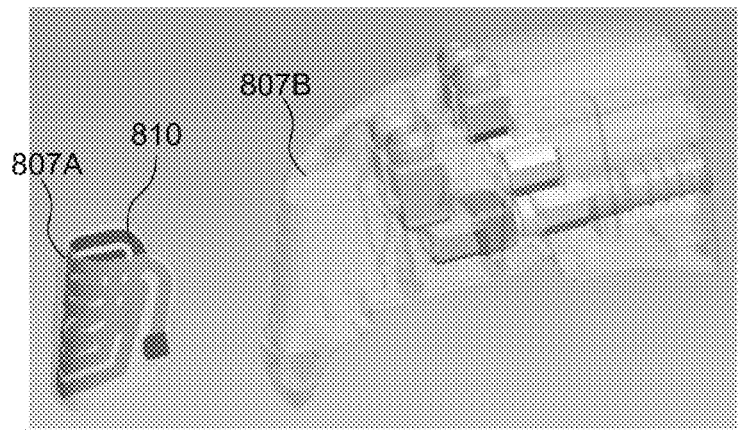
Figure 8C:
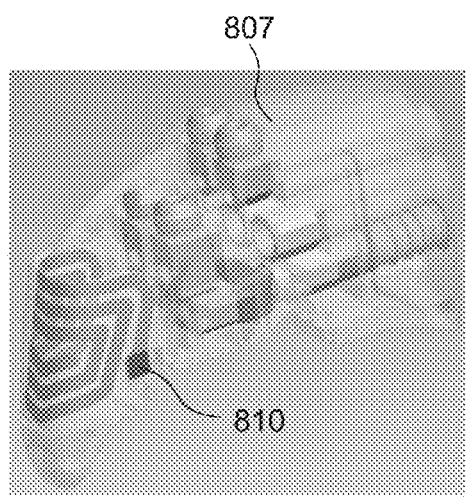

FIGS. 8A-C illustrate generally an example of an apparatus that can include a modular implantable antenna assembly. In an example, an IMD can include a first dielectric portion 807A, and a second dielectric portion 807B, and a dielectric compartment 807. The second dielectric portion 807B can include a header the IMD, such as configured for attachment to a conductive housing. For example, the header can provide one or more mechanical or electrical connections to one or more implantable lead assemblies, An implantable antenna including a spiral conductor 810 can be located in an otherwise unused portion of the header.

In an example, the first dielectric portion 807A can be a dielectric shell, such as including an interior-facing surface sized and shaped to accommodate the spiral conductor 810. For example, the first portion 807A can include one or more cavities, slots, stakes, ridges or other structures such as to provide or maintain a desired spacing or geometry for the spiral conductor 810, such as to avoid deforming the spiral conductor 810 in an unwanted manner during manufacturing.

In the example of FIG. 8A, the first dielectric portion 807A can be configured to have two substantially parallel interior faces (e.g., vertical sidewalls), and a portion extending between the two substantially parallel interior faces (e.g., the rear portion), to provide a "u"-shaped shell. In an example, the spiral conductor 810 can be inserted into or otherwise attached to the interior-facing surface of the u-shaped first dielectric portion 807A, such as using an injection (e.g., insert molding process).

In an examples of FIGS. 8B-C, the combination of the spiral conductor 810 and the first dielectric portion 807A can then be attached to a desired location on the second dielectric portion 807B (e.g., such as using a medical adhesive including silicone, or using an overmolding process, or one or more other techniques). For example, use of the modular assembly technique as shown in FIG. 8 can provide a desired separation between the spiral conductor 810 and a conductive housing 805 of the IMD.

Figure 9:
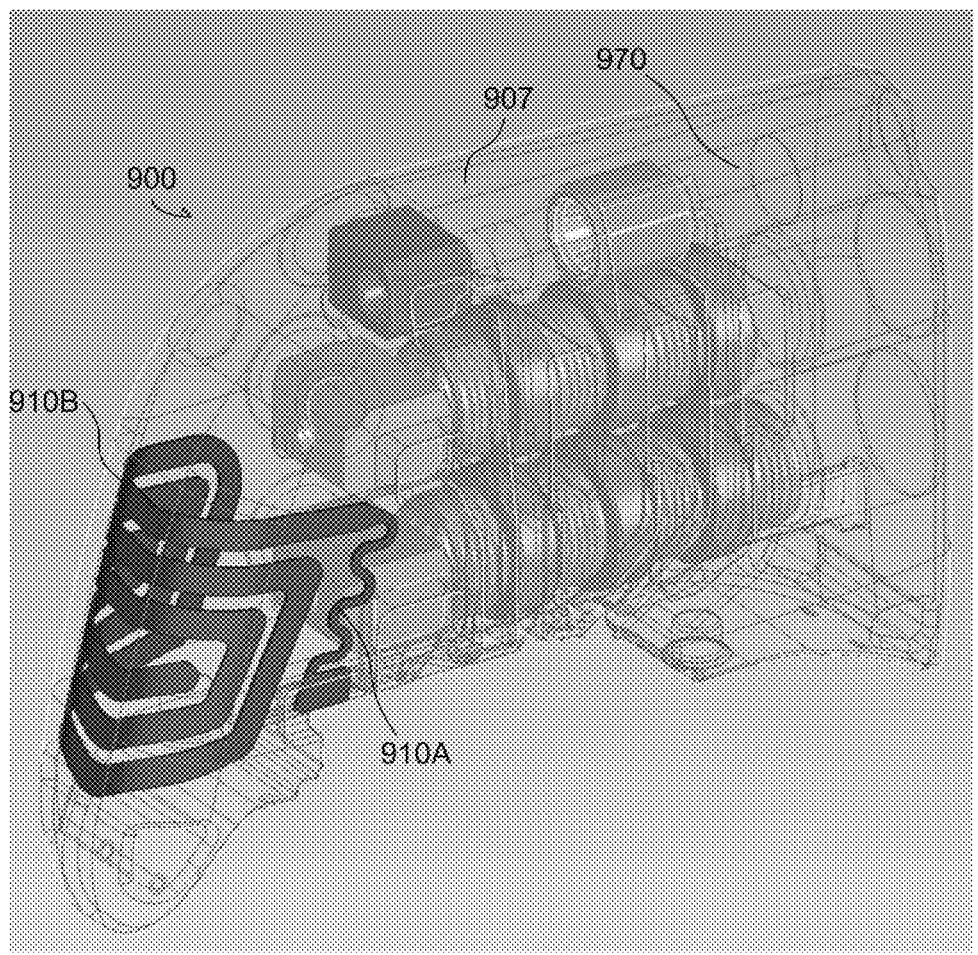
FIG. 9 illustrates generally an example of an apparatus that can include an implantable antenna comprising a loading portion.

FIG. 9 illustrates generally an example of an apparatus 900 that can include an implantable antenna comprising a loading portion 910A, and a spiral conductor portion 910B, such as located within a dielectric material 907. In an example, the dielectric compartment 907 can be a header attached to an IMD housing, as discussed in the examples above, such as including a lead bore 970 configured to receive an implantable lead assembly. In the example of FIG. 9, the loading portion 910A can include a different conductor cross section than the spiral conductor portion 910B, such as to adjust an input impedance of the implantable antenna to achieve a specified input impedance range within a specified operating frequency range. For example, the spiral conductor portion 910B can provide an input impedance in both free space and in vivo that includes a relatively large capacitive component. The loading portion 910A can be used, at least in part, to reduce such a capacitive component of the input impedance. In an example, the loading portion 910A can include one or more other conductor shapes or configurations, such as a coil, a helix, a conductive segment oriented vertically with respect to the housing of the IMD, or one or more other conductor shapes, cross sections, or orientations. In an example, the spiral conductor portion 910B can instead be replaced with one or more other conductor geometries, such as a serpentine conductor shown in the example of FIG. 3B.

In the example of FIG. 9, one or more adjacent segments in the spiral conductor portion can be offset in depth from one another, such as discussed in the examples of FIGS. 5A-C. For example, such an offset in depth can help reduce an unwanted capacitive interaction between adjacent segments due at least in part to a fringing field effect.

Figure 10A:
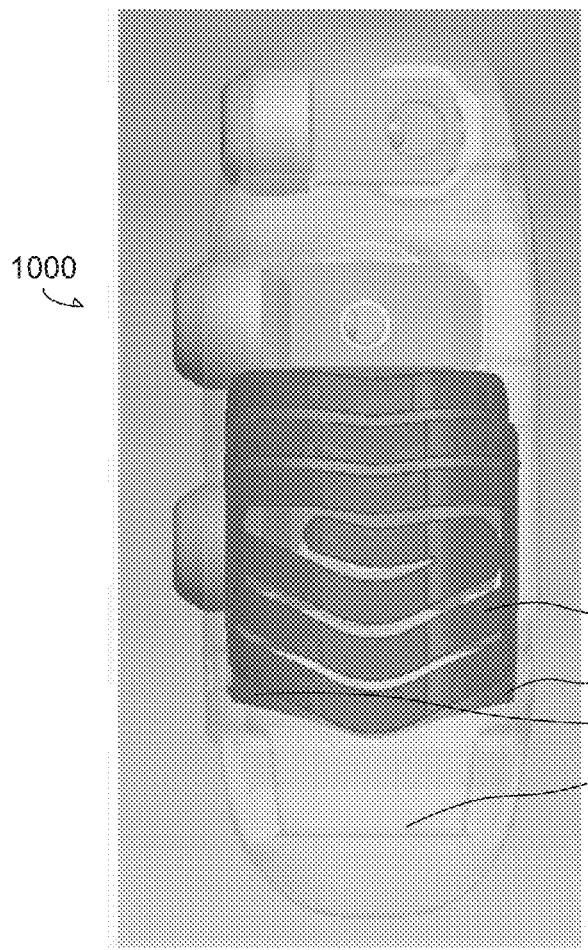
FIGS. 10A-B illustrate generally an example of an apparatus that can include an implantable antenna including a spiral conductor.
Figure 10B:
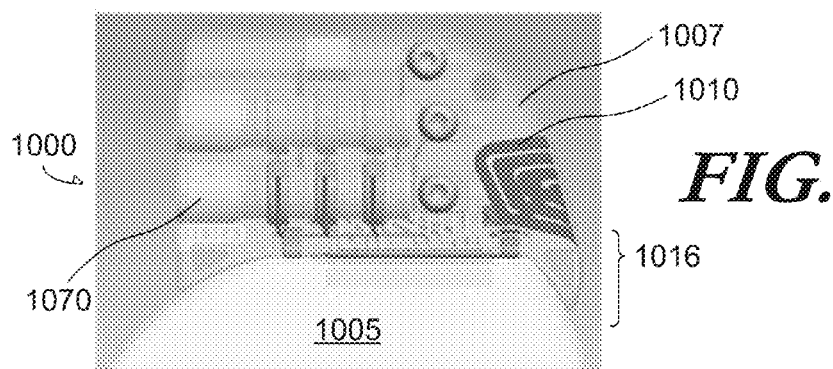

FIGS. 10A-B illustrate generally an example of an apparatus 1000 that can include an implantable antenna 1010 that can include a spiral conductor. In the examples of FIGS. 10A-B, the spiral conductor can be located within a dielectric compartment 1007 (e.g., a header of an IMD), such as in a region not otherwise occupied by or near a lead bore 1070 or associated mechanical features (e.g., away from one or more contacts associated with a lead connector assembly, or away from a set-screw assembly, etc.). In an example, such as shown in FIG. 10B, the antenna 1010 can be shaped or formed so that a specified separation is maintained between the antenna 1010 conductor, and a nearby conductor such as a housing of the IMD, such as shown near the region 1016. Such a configuration can provide less electrical loading of the antenna 1010 by the housing 1005, as compared to an antenna including a portion as shown in the shaded regions 1017A-B.

FIGS. 11-18 generally show various illustrative examples of apparatuses 1100, 1200, 1300, 1400, 1500, 1600, 1700, and 1800 that can include a respective implantable antenna 1110, 1210, 1310, 1410, 1510, 1610, 1710, or 1810 including a spiral conductor, the spiral conductor sized and shaped to provide specified electrical operating characteristics within a specified operating frequency range, the examples including various dielectric compartment and housing configurations, such as included as a portion or part of an IMD.

In the examples of FIGS. 11-18, an IMD housing 1105, 1205, 1305, 1405, 1505, 1605, 1705, or 1805 can include a conductive portion, such as a hermetically-sealed, laser-welded titanium enclosure, such as containing one or more circuit assemblies. Such circuit assemblies can include one or more electrostimulation or physiologic sensing circuits, such as coupled to one or more implantable lead assemblies via a connector assembly 1170, 1270, 1370, 1470, 1570, 1670, 1770, or 1870, located within or as a portion of a dielectric compartment 1107, 1207, 1307, 1407, 1507, 1607, 1707, or 1807. In the examples of FIGS. 1-18, various dielectric compartment configurations can be used, such as determined by how many implantable lead assemblies will be used (if any). Also, a number of electrodes or a number of lead wires included in a respective lead assembly can vary from one dielectric compartment 1107, 1207, 1307, 1407, 1507, 1607, 1707, or 1807 to another. For example, a multi-polar lead connector can provide respective connections within the dielectric compartment 1107, 1207, 1307, 1407, 1507, 1607, 1707, or 1807 to respective conductors connected to various electrical inputs or outputs of circuitry within the housing (e.g. via a hermetically-sealed filtered feedthrough assembly). The present inventors have also recognized that using an antenna with a spiral conductor configuration "tucked" into otherwise unused space in the dielectric compartment 1107, 1207, 1307, 1407, 1507, 1607, 1707, or 1807 may allow a common antenna design to be used across different dielectric compartment or housing configurations, such as reducing manufacturing complexity or increasing design flexibility.

In the examples of FIGS. 11-18, one or more physical parameters of the spiral conductor can be adjusted, such as to provide specified electrical operating characteristics within a specified operating frequency range. As in the examples of FIGS. 5A-C, a number of turns of the spiral conductor, the lateral width of the spiral conductor, the sidewall height of the spiral conductor, a separation between adjacent turns of the spiral conductor, a path length along the spiral conductor, a total surface area of the antenna 1110, 1210, 1310, 1410, 1510, 1610, 1710, or 1810, a diameter of a hypothetical sphere sized to enclose the antenna 110, 1210, 1310, 1410, 1510, 1610, 1710, or 1810, or a separation between an end and an initial location along the antenna 1110, 1210, 1310, 1410, 1510, 1610, 1710, or 1810 can affect various electrical characteristics of the antenna 1110, 1210, 1310, 1410, 1510, 1610, 1710, or 1810. Such electrical characteristics can include a total radiated power (TRP), a radiation an efficiency, a directivity, or an input impedance, either in free space (e.g., air), or after implant in tissue. For example, TRP can be determined with respect to a reference power level, such as 1 milliwatt, and simulated or measured in decibel (e.g., logarithmic) units (e.g., dBm). Similarly, the directivity can be determined relative to an isotropic radiator, and simulated or measured in decibel units (e.g., dBi).

The illustrative examples of FIGS. 11-18 can be simulated using an electromagnetic modeling software package, such as Microwave Studio®, provided by Computer Simulation Technology, CST AG, Darmstadt, Germany. For example, TABLE 1, below, includes results of simulation performed on the illustrative examples of FIGS. 11-18 to estimate various antenna 1110, 1210, 1310, 1410, 1510, 1610, 1710, or 1810 electrical performance characteristics. Similarly, TABLE 2 illustrates generally various antenna conductor dimensions corresponding to the various illustrative examples provided in TABLE 1.

TABLE 1

Antenna Simulation Results for Various Illustrative Examples

Figure 11:
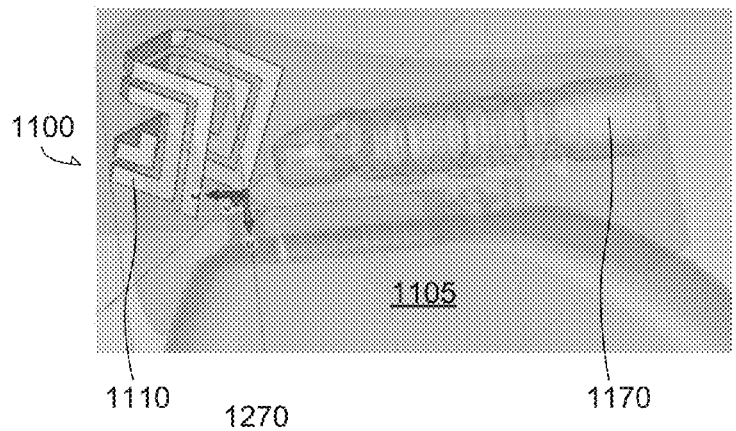
FIGS. 11-18 illustrate generally examples of an apparatus that can include an implantable antenna including a spiral conductor, the spiral conductor sized and shaped to provide specified electrical operating characteristics within a specified operating frequency range, the examples including various dielectric compartment and housing configurations.
Figure 12:
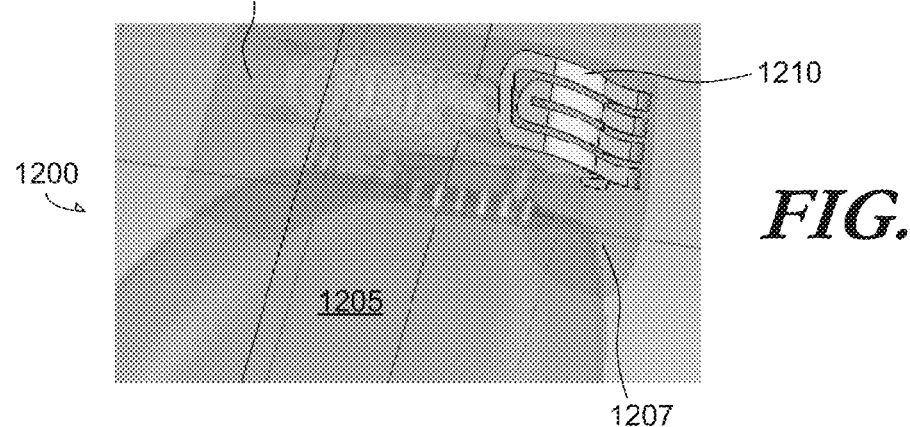
Figure 13:
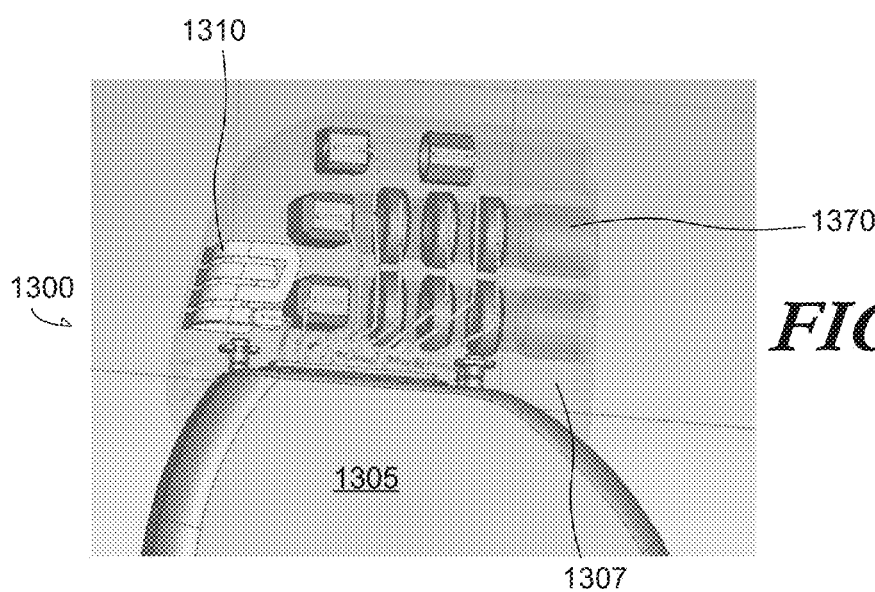
Figure 14:
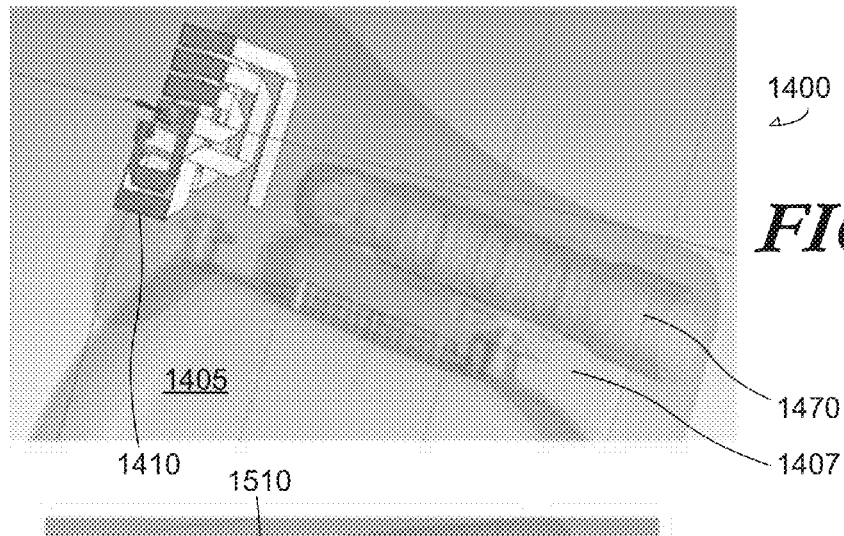
Figure 15:
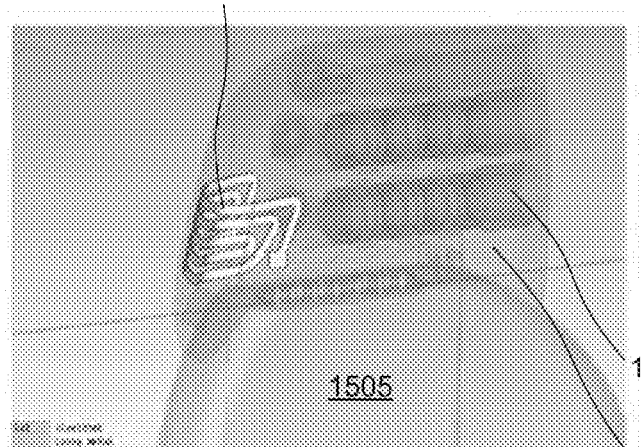
Figure 16:
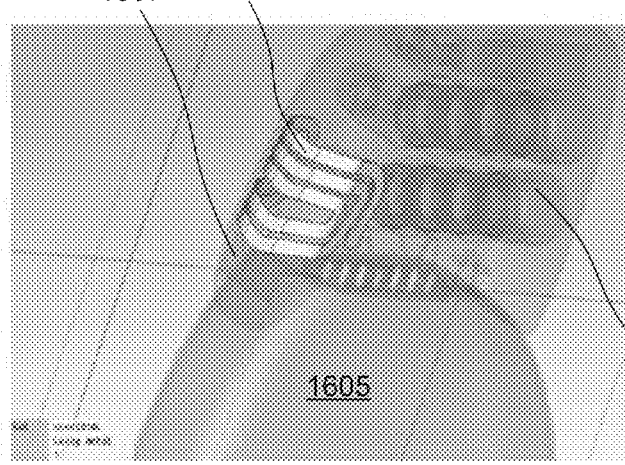
Figure 17:
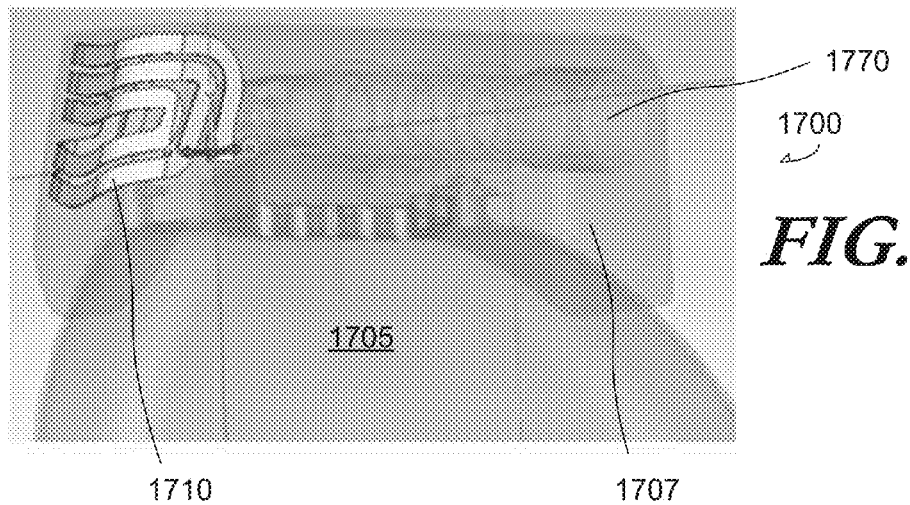
Figure 18:
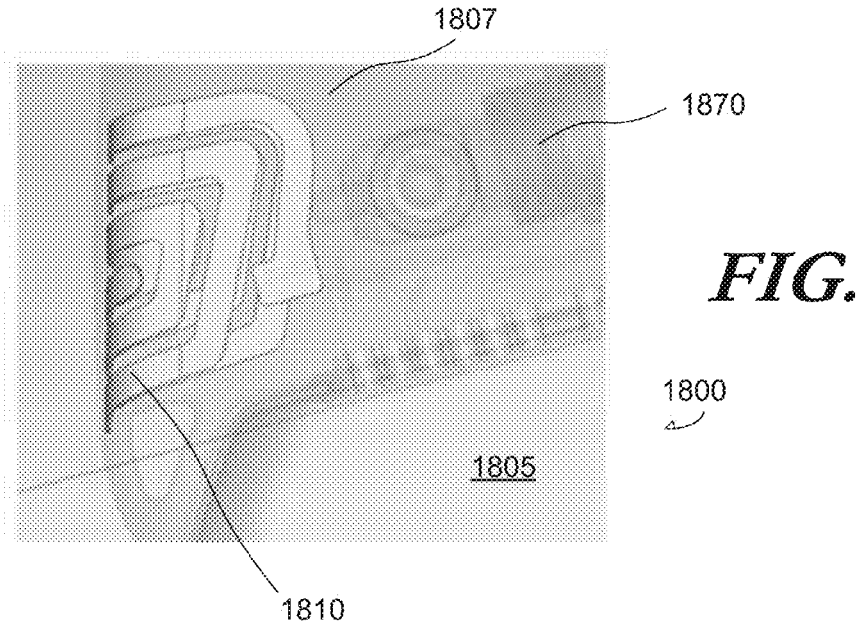

| Example | Impedance - Air (Ohms) | TRP - Air (dBm) | Directivity - Air (dBi) | Impedance - in vivo (Ohms) | TRP - in vivo (dBm) | Directivity - in vivo (dBi) |
|---|---|---|---|---|---|---|
| FIG. 11 | 7 - j120 | −27 | 1.9 | 25 - j30 | −23 | 2.12 |
| FIG. 12 | 7 - j135 | −33 | 1.85 | 22 - j51 | −27 | 2.25 |
| FIG. 13 | 9 - j150 | −36 | 1.85 | 22 - j66 | −29 | 2.27 |
| FIG. 14 | 8.5 - j135 | −28 | 1.87 | 26 - j41 | −25 | 2.15 |
| FIG. 15 | 9 - j147 | −36 | 1.88 | 27 - j54 | −28 | 2.4 |
| FIG. 16 | 9 - j134 | −35 | 1.89 | 27 - j42 | −27 | 2.4 |
| FIG. 17 | 8 - j135 | −33 | 1.88 | 23 - j37 | −26 | 2.3 |
| FIG. 18 | 9 - j140 | −34 | 1.88 | 34 - j25 | −25 | 2.3 |

TABLE 2

Antenna Conductor Dimensions

| Example | Ribbon Width - "w" (mils) | Spacing between turns - "d" (mils) | Total ribbon length (inches) |
|---|---|---|---|
| FIG. 11 | 50 | 20 | 4.14 |
| FIG. 12 | 50 | 20 | 3.25 |
| FIG. 13 | 50 | 20 | 3.25 |
| FIG. 14 | 45 | 15 | 4.8 |
| FIG. 15 | 34 | 15 | 4 |
| FIG. 16 | 45 | 15 | 3.8 |
| FIG. 17 | 45 | 20 | 3.8 |
| FIG. 18 | 45 | 20 | 4.5 |

FIGS. 19A-B, 20A-B, 21A-B illustrate generally examples of an apparatus 1900, 2000, or 2100, that can include an implantable antenna 1910B, 2010B, or 2110B including a spiral conductor 1910A, 2010A, or 2110A, the spiral conductor sized and shaped to provide specified electrical operating characteristics within a specified operating frequency range, the examples including various dielectric compartment and housing configurations. In the illustrative examples of FIGS. 19A-B, 20A-B, and 21A-B, the spiral conductor 1910A, 2010A, or 2110A can be etched, stamped or otherwise formed (such as shown in the examples of FIGS. 7A-C and elsewhere) to provide a substantially planar conductor, such as including a ribbon-shaped conductor cross section. A portion 1919, 2019, or 2119 of the spiral conductor 1910A, 2010A, or 2110A can be sized and shaped to provide an electrical attachment or bonding point, such as to allow an electrical coupling to be made between the antenna 1910B, 2010B, or 2110B and circuitry within a housing 1905, 2005, or 2105 of an IMD.

In an example, the antenna 1910B, 2010B, or 2110B can be folded or otherwise formed into a desired configuration, such as located within a dielectric compartment 1907, 2007, or 2107 away from one or more electrical connectors for one or more implantable lead assemblies, such as a first lead bore 1970, 2070, or 2170. In an example, such as shown in FIGS. 19B, 20B, and 21B, the antenna 1910B, 2010B, or 2110B can substantially conform to the contour of one or more exterior faces of the dielectric compartment 1907, 2007, or 2107, such as to maintain a specified depth within the compartment, or to maintain a specified separation between the housing 1905, 2005, or 2105 and the antenna 1910B, 2010B, or 2110B.

Figure 19A:
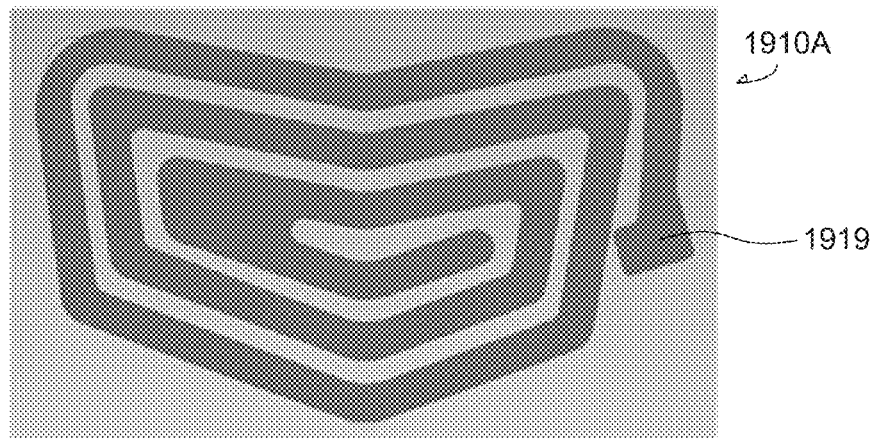
FIGS. 19A-B, 20A-B, 21A-B illustrate generally examples of an apparatus that can include an implantable antenna including a spiral conductor, the spiral conductor sized and shaped to provide specified electrical operating characteristics within a specified operating frequency range, the examples including various dielectric compartment and housing configurations.
Figure 19B:
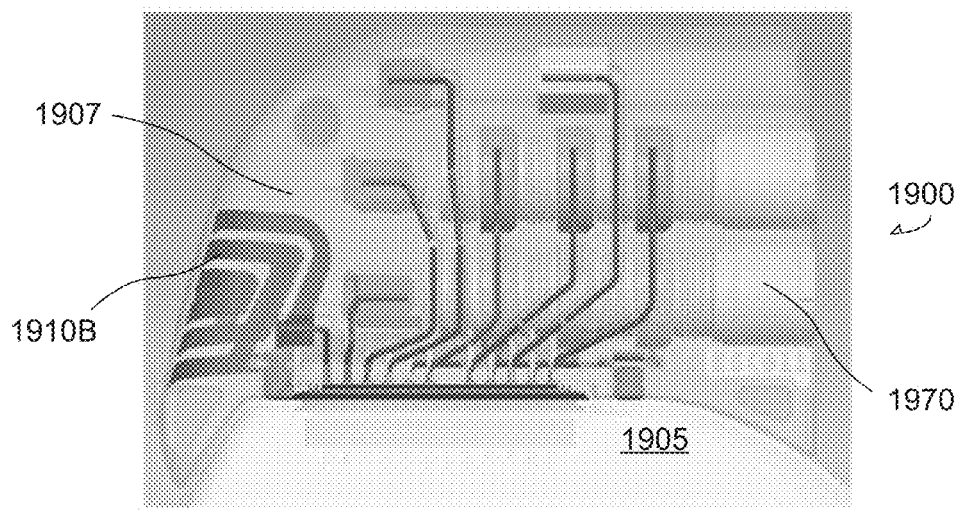
Figure 20A:
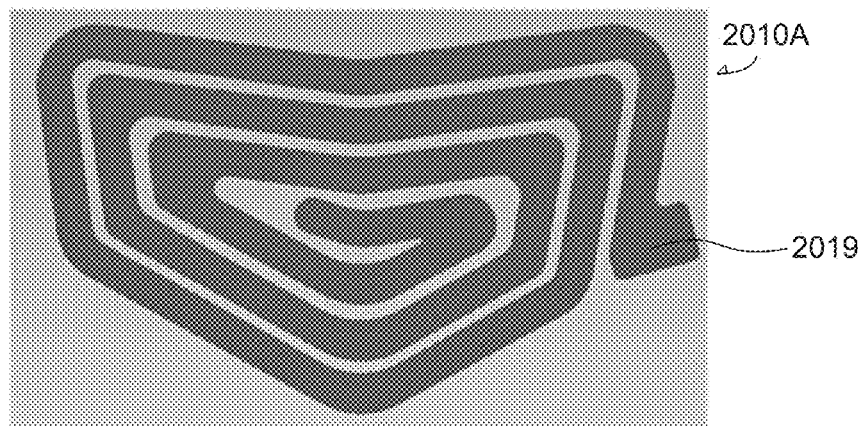
Figure 20B:
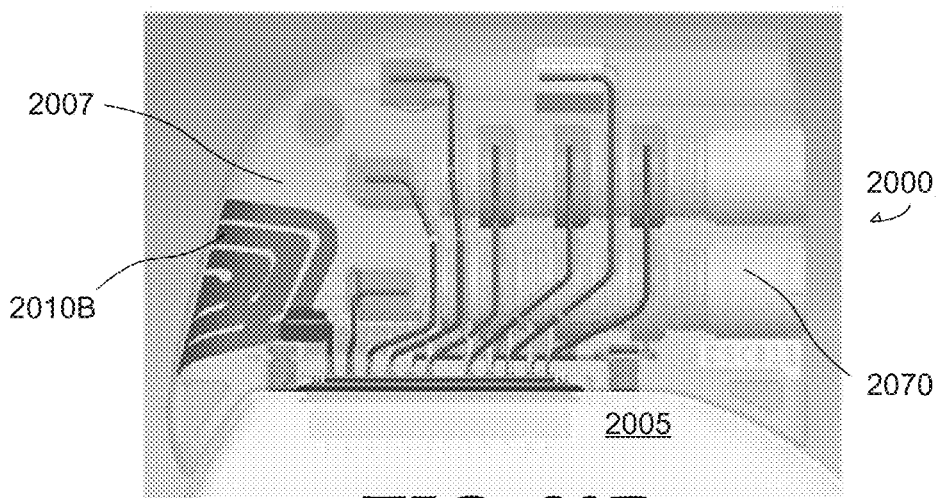
Figure 21A:
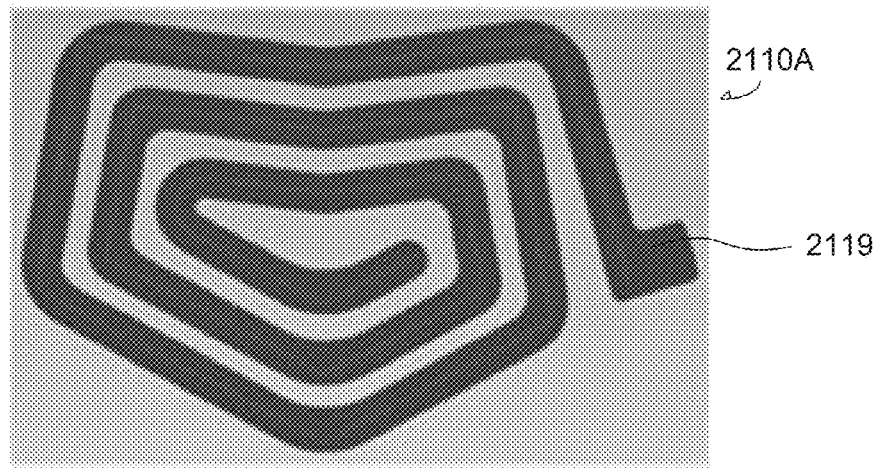
Figure 21B:
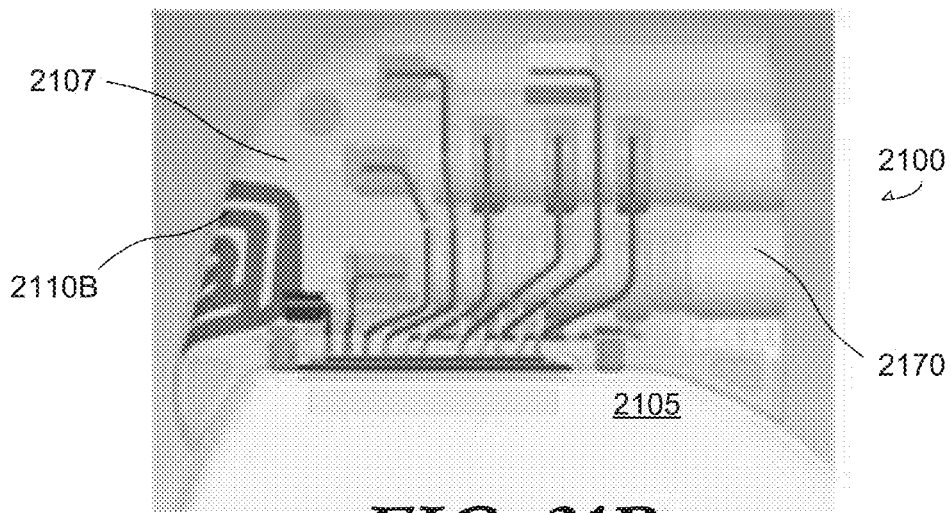

In the example of FIG. 20B, the antenna 2010B is spaced slightly further away from the housing 2005 as compared to the example of FIG. 19B. Similarly, in the example of FIG. 21B, the antenna 2110B is spaced slightly further away from the lead connectors, such as the first lead bore 2170, as compared to the examples of FIGS. 19B and 20B. TABLE 3 illustrates generally various antenna simulation results and physical dimensions corresponding to the antennas 1910B, 2010B, and 2110B of FIGS. 19B, 20B, and 21B. In the illustrative examples of FIGS. 20B-21B, the spacing between adjacent turns, "d," can taper or vary along the path of the antenna 2010B, or 2110B, thus a range of values are included in TABLE 3.

TABLE 3

Antenna Simulation Results and Dimensions for Various Illustrative Examples

| Example | TRP - Air (dBm) | TRP - in vivo (dBm) | Ribbon Width - "w" (mils) | Spacing between turns - "d" (mils) | Total ribbon length (inches) | Overall height (inches) |
|---|---|---|---|---|---|---|
| FIG. 19B | −34 | −25 | 45 | 25 | 4.514108 | 0.478 |
| FIG. 20B | −34 | −26 | 45 | 12.5-15 | 4.460559 | 0.48 |
| FIG. 21B | −35 | −28 | 45 | 21.5-25 | 3.876241 | 0.483 |

Figure 22:
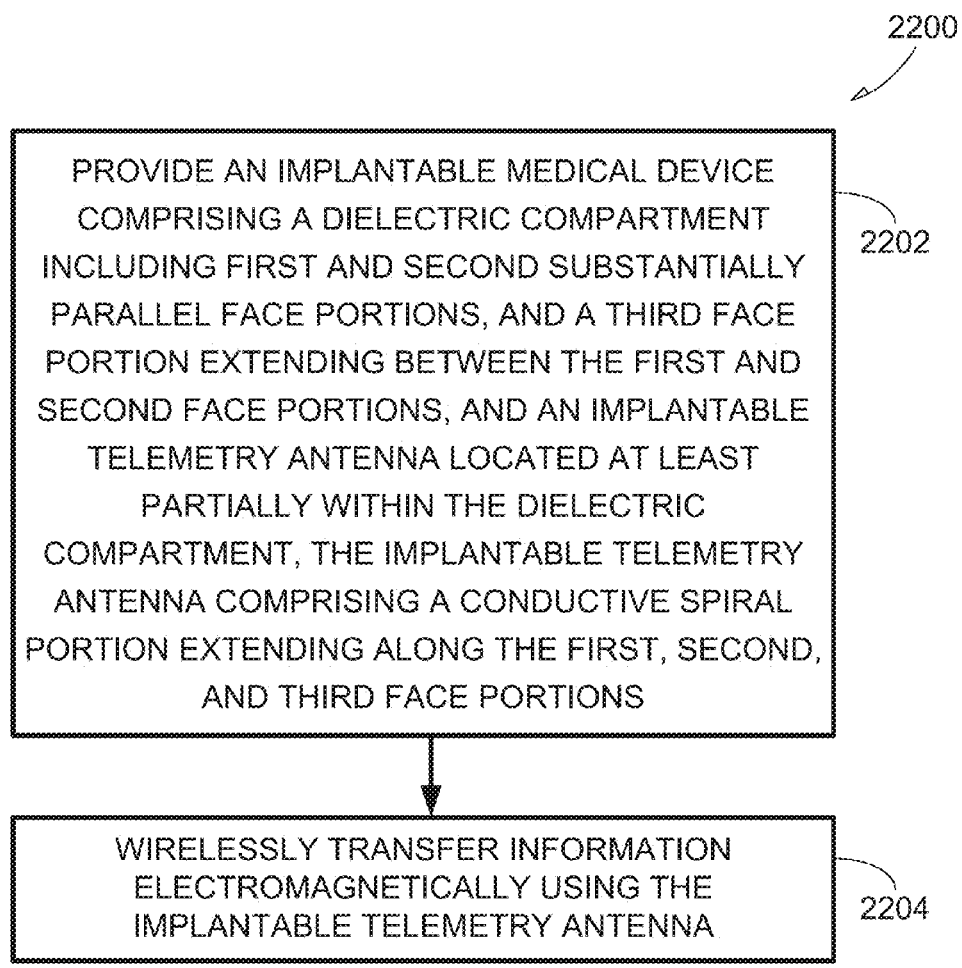
FIG. 22 illustrates generally an example of technique that can include providing an implantable medical device including an implantable telemetry antenna, and wirelessly transferring information electromagnetically using the implantable telemetry antenna.

FIG. 22 illustrates generally an example of technique 2200 that can include, at 2202, providing an implantable medical device including an implantable telemetry antenna, such as shown in one or more of the examples of the previous figures. At 2204, the technique 2200 can include wirelessly transferring information electromagnetically using the implantable telemetry antenna, such as shown in the examples of FIGS. 1-2, for an implantable antenna included as a portion of an IMD.

Figure 23A:
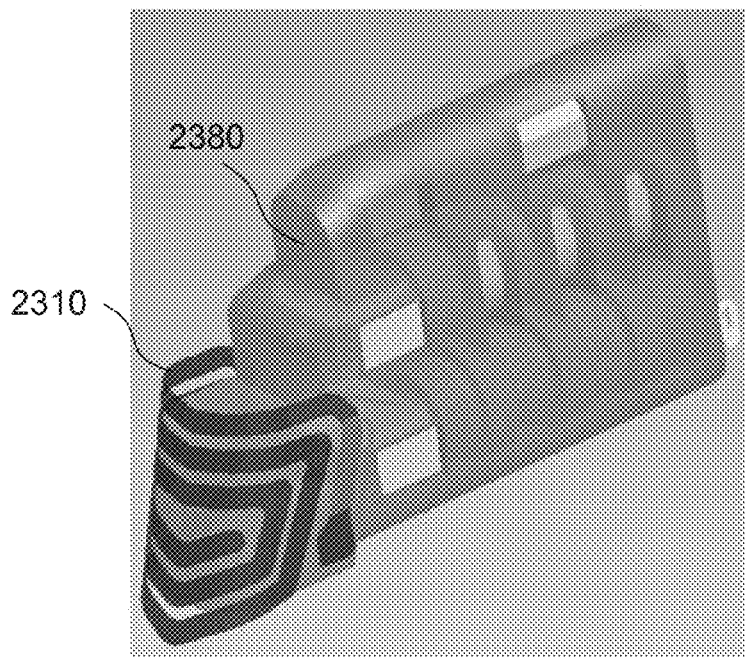
FIGS. 23A-B illustrate generally an example of an apparatus that can include a modular implantable antenna assembly.
Figure 23B:
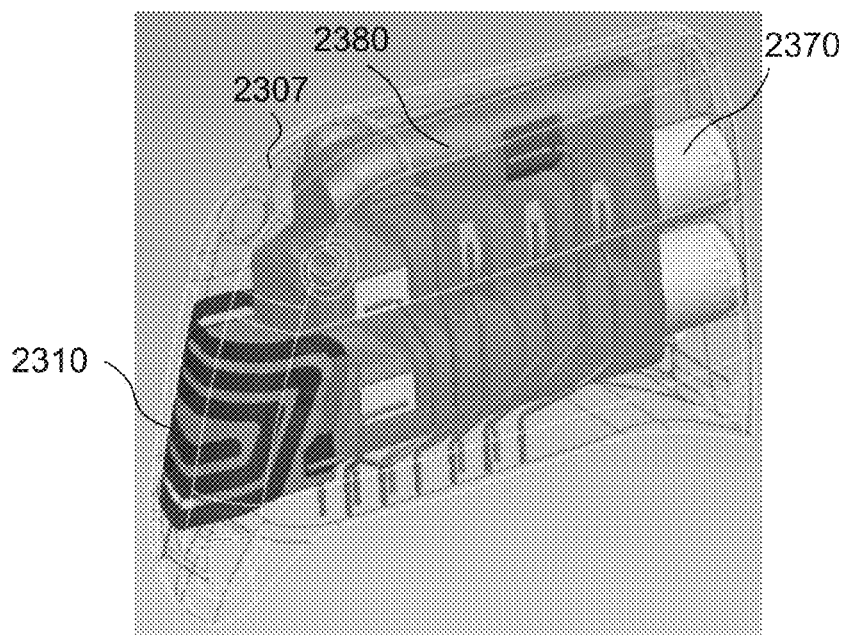

FIGS. 23A-B illustrate generally an example of an apparatus that can include a modular implantable antenna assembly. In the example of FIG. 23A, a dielectric core 2380 can be formed, such as injection molded using an epoxy or urethane compound. A portion of the dielectric core 2380 can be insert-molded or otherwise formed to include one or more set-screw blocks or other structures. For example, a spiral conductor 2310 can form a portion of an antenna, such as discussed in the examples above. A portion of the dielectric core 2380 can be insert-molded or otherwise bonded to mechanically retain the spiral conductor 2310. Then, a dielectric compartment 2307 can be overmolded or otherwise formed to contain the dielectric core 2380, and the spiral conductor 2310, such as to provide an implantable assembly. For example, the implantable assembly shown in FIG. 23B can include a header, such as to provide an electrical or mechanical connection to one or more implantable leads, such as via a lead cavity or "bore" 2370. Such a header can then be mechanically attached to an implantable medical device housing, as discussed in the examples above. In the example of FIGS. 23A-B, the dielectric core can include two substantially parallel face portions, such as in the side-wall regions of the core 2380. The spiral conductor can be conformed or otherwise shaped to extend along a portion of the two substantially parallel faces as shown in FIGS. 23A-B, and a central portion of the spiral conductor 2310 can extend along a surface of the core 2380, such as comprising a third face extending between the two side-wall regions of the core 2380. Such a configuration provides a more omni-directional antenna configuration while still efficiently using the available volume within the dielectric compartment 2307. In an example, the dielectric core 2380 can include a channel or one or more stakes, such as to retain or immobilize the spiral conductor 2310 prior, during, or after a molding operation or one or more other fabrication steps. In a stake example, the spiral conductor 2310 can include a hole or one or more other structures, and a stake can penetrate through or can otherwise retain the spiral conductor 2310, such as after the stake is pressed or deformed, using either acoustic energy, heat, or one or more other techniques.

Figure 24A:
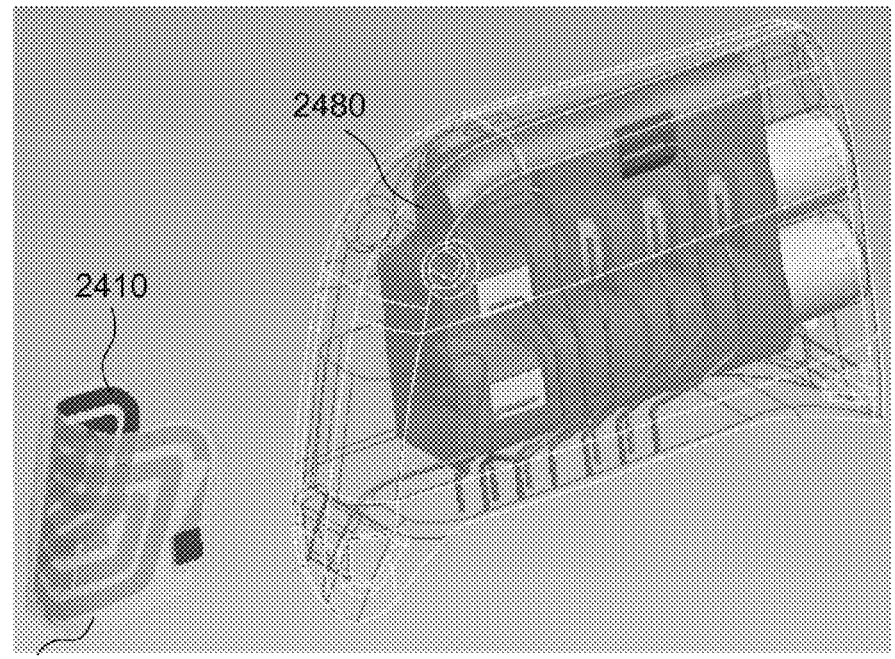
FIGS. 24A-B illustrate generally an example of an apparatus that can include a modular implantable antenna assembly.
Figure 24B:
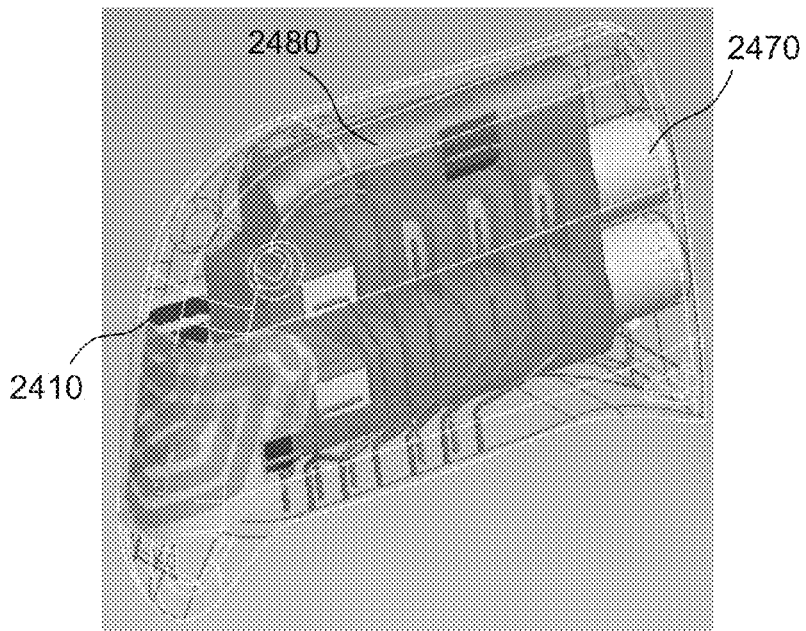

FIGS. 24A-B illustrate generally an example of an apparatus that can include a modular implantable antenna assembly. In the example of FIG. 24A, similar to the example of FIG. 23A, a dielectric core 2480 can be formed, such as injection molded or insert-molded to include one or more set-screw blocks or other structures. Then, a dielectric compartment 2407A can be overmolded or otherwise formed around the dielectric core. Unlike the example of FIGS. 23A-B, a module implantable antenna assembly can be configured similarly to the examples of FIGS. 8A-C. For example, the dielectric compartment 2407A can include a cavity, a channel, or a general area where a dielectric shell 2407A can be attached. In an example, the dielectric shell 2407A can be "U"-shaped, such as including an exterior-facing portion, and an interior-facing portion. In the example of FIG. 24A, the spiral conductor 2410 (such as a portion of an implantable antenna assembly) can be located on the interior-facing portion of the dielectric shell 2407A. In an example, the dielectric shell 2407A can be insert-molded around the spiral conductor 2410, such as to retain the antenna 2410. Then, in the example of FIG. 24B, similarly to the examples of FIGS. 8A-C, the combination of the dielectric shell 2407A and the spiral conductor 2410 can be attached to the dielectric compartment 2480, such as to immobilize the spiral conductor 2410. As in the examples above, the dielectric compartment can be a header configured to provide an electrical or mechanical connection to one or more implantable leads, such as via a lead bore 2470. As with all the examples discussed above and below, the dielectric compartment 2480 need not be homogeneous or all-dielectric throughout its entire volume. For example, in FIG. 24B, one or more set-screw blocks, connecting wires, or other structures can be included within the dielectric compartment. In an example, a portion of the dielectric compartment 2480 can be hollow or can include a cavity or a channel. Such a cavity or a channel can initially be open, but can be later filled or overmolded with dielectric material such as an adhesive, a back-fill material, or one or more other materials, such as after making one or more internal electrical or mechanical connections, or such as after attachment of the dielectric shell 2407A to the dielectric compartment 2480.

Figure 25A:
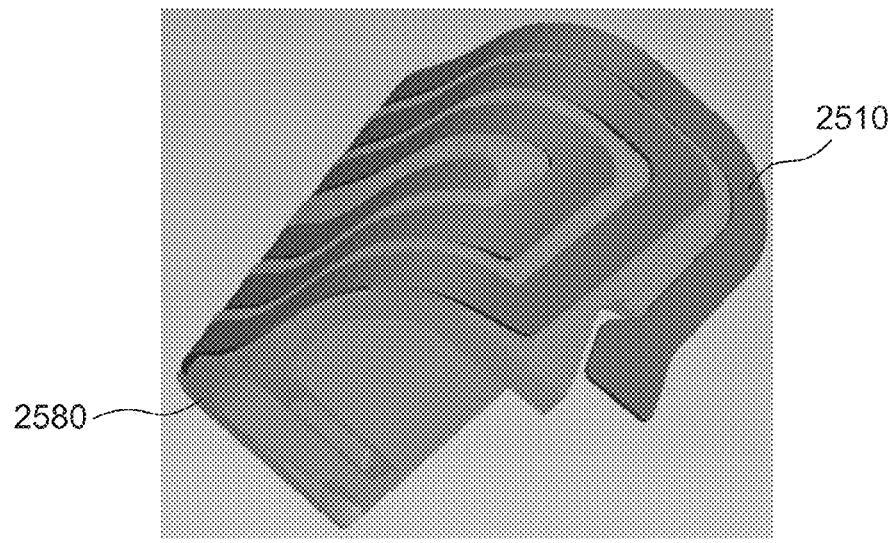
FIGS. 25A-B illustrate generally an example of an apparatus that can include a modular implantable antenna assembly.
Figure 25B:
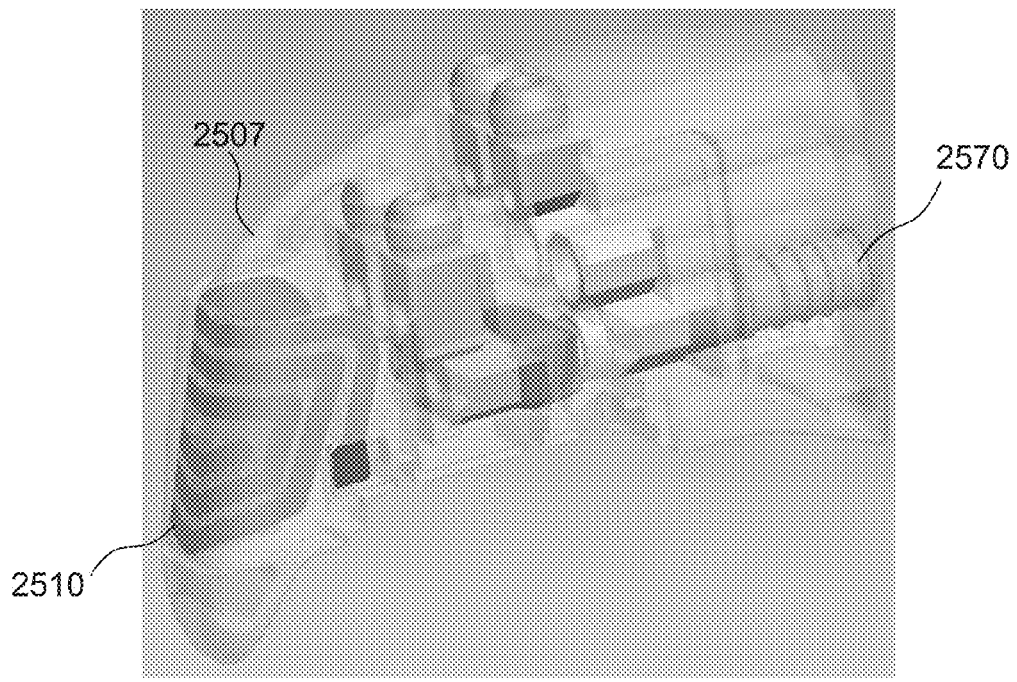

FIGS. 25A-B illustrate generally an example of an apparatus that can include a modular implantable antenna assembly. In FIG. 25A, a dielectric core 2580 can be formed, such as molded or otherwise fabricated to include a cavity or channel. The cavity or channel can be sized and shaped to complement a spiral conductor 2510, such as to retain or align the spiral conductor 2510. In an example, the core 2580 can be insert-molded around a portion of the spiral conductor 2510. In an example, the core can include a stake or other structure. Such a stake or other structure can be used to attach the spiral conductor 2510 to the core. In the example of FIG. 25B, a dielectric compartment 2507 can contain the dielectric core 2580 and spiral conductor 2510. For example, the dielectric compartment 2507 can be formed by overmolding the dielectric core 2580, or by placing the antenna assembly comprising the core 2580 and spiral conductor 2510 into a cavity within the dielectric compartment 2507, and then backfilling any remaining space in the cavity with medical adhesive or one or more other compounds. The dielectric compartment 2507 can include one or more other structures, such as a set screw block or other mechanical or electrical connections, such as to provide an interface for an implantable lead via a lead connector 2570.

In the examples of FIGS. 23A-B, 24A-B, and 25A-B, similar to the examples of FIGS. 8A-C, a modular antenna assembly can be fabricated, such as tailored to a specific location of use (e.g., for use at a specified range of frequencies, or for use with a particular model of implantable medical device). Such a modular assembly can allow an antenna configuration to be specified or selected for use with a specified implantable medical device assembly (e.g., pairing a particular antenna assembly to a desired implantable medical device configuration, such as during manufacturing). Also, such a modular design can allow revision to the antenna assembly, such as to the spiral conductor, without requiring the rest of the dielectric compartment design to change, reducing the cost of development.

Various Examples

Example 1 includes subject matter (such as an apparatus) comprising an implantable medical device, including a housing, an implantable telemetry circuit carried within the housing, a dielectric compartment, mechanically coupled to the housing, the dielectric compartment including first and second substantially parallel face portions and a third face portion extending between the first and second face portion, an implantable telemetry antenna, located at least partially within the dielectric compartment. In Example 1, the implantable telemetry circuit is electrically coupled to the implantable telemetry antenna and configured to wirelessly transfer information electromagnetically using the implantable telemetry antenna, the implantable telemetry antenna comprises a spiral conductor portion extending along the first, second, and third face portions.

In Example 2, the subject matter of Example 1 can optionally include a spiral conductor comprising a planar spiral pattern including concentric turns, the planar spiral pattern folded so that respective portions of the planar spiral pattern are located near, and are substantially parallel to, the first and second face portions of the dielectric compartment.

In Example 3, the subject matter of one or any combination of Examples 1-2 can optionally include an implantable telemetry antenna comprising a loading portion, coupled to the spiral conductor and the implantable telemetry circuit, the loading portion configured to adjust an input impedance of the implantable telemetry antenna, to provide a specified input impedance range within a specified range of operating frequencies to be used for wireless information transfer.

In Example 4, the subject matter of one or any combination of Examples 1-3 can optionally include a loading portion comprising a conductive segment substantially perpendicular to a surface of the housing, the conductive segment of the loading portion configured to adjust the input impedance of the implantable telemetry antenna by reducing or about canceling a capacitive portion of the input impedance of the implantable telemetry antenna.

In Example 5, the subject matter of one or any combination of Examples 1-4 can optionally include a dielectric compartment of the implantable medical device comprising a header configured to provide an electrical and mechanical connection to an implantable lead, the implantable lead including an electrode configured for location at a tissue site, and coupled to electronic circuitry within the housing to provide one or more of electrostimulation of tissue, or sensing of activity, at the site of the electrode.

In Example 6, the subject matter of one or any combination of Examples 1-5 can optionally include an implantable lead and the electrode.

In Example 7, the subject matter of one or any combination of Examples 1-6 can optionally include a spiral conductor including a cross section having a lateral width that is greater than a sidewall height of the cross section.

In Example 8, the subject matter of one or any combination of Examples 1-7 can optionally include a portion of the spiral conductor located toward the housing and oriented so that the sidewall provides a face located near the housing that is substantially parallel to a surface of the housing.

In Example 9, the subject matter of one or any combination of Examples 1-8 can optionally include a separation between adjacent turns of the spiral conductor decreased as compared to using a cross section lacking the lateral width greater than the sidewall height to provide a specified input impedance range within the specified range of operating frequencies.

In Example 10, the subject matter of one or any combination of Examples 1-9 can optionally include a total surface area of the implantable telemetry antenna increased as compared to using a cross section lacking the lateral width greater than the sidewall height to provide a specified input impedance range within the specified range of operating frequencies.

Example 11 includes subject matter (such as an apparatus) comprising an implantable medical device including a housing, an implantable telemetry circuit carried within the housing, a dielectric compartment, mechanically coupled to the housing, an implantable telemetry antenna located at least partially within the dielectric compartment, the implantable telemetry circuit electrically coupled to the implantable telemetry antenna and configured to wirelessly transfer information electromagnetically using the implantable telemetry antenna. In Example 11, the implantable telemetry antenna comprises a spiral conductor extending along a face portion of the dielectric compartment, the conductor including a cross section having a lateral width that is greater than a sidewall height of the cross section, and one or more of a number of turns of the spiral conductor, the lateral width of the spiral conductor, the sidewall height of the spiral conductor, a separation between adjacent turns of the spiral conductor, a path length along the spiral conductor, a total surface area of the antenna, a diameter of a hypothetical sphere sized to enclose the antenna, or a separation between an end and an initial location along the antenna, is used to provide a specified input impedance range, within a specified range of operating frequencies to be used for wireless information transfer.

In Example 12, the subject matter of Example 11 can optionally include a separation between adjacent turns of the spiral conductor decreased as compared to using a cross section lacking the lateral width greater than the sidewall height to provide the specified input impedance range within the specified range of operating frequencies.

In Example 13, the subject matter of one or any combination of Examples 11-12 can optionally include a total surface area of the implantable telemetry antenna increased as compared to using a cross section lacking the lateral width greater than the sidewall height to provide the specified input impedance range within the specified range of operating frequencies.

In Example 14, the subject matter of one or any combination of Examples 11-13 can optionally include a spiral conductor comprising a planar spiral pattern including concentric turns, the planar spiral pattern folded so that at least a portion of the planar spiral pattern is parallel to the face portion of the dielectric compartment.

In Example 15, the subject matter of one or any combination of Examples 11-14 can optionally include an implantable telemetry antenna including a loading portion, coupled to the spiral conductor and the implantable telemetry circuit, the loading portion configured to adjust an input impedance of the implantable telemetry antenna, to provide a specified input impedance range within a specified range of operating frequencies to be used for wireless information transfer.

In Example 16, the subject matter of one or any combination of Examples 11-15 can optionally include a loading portion comprising a conductive segment substantially perpendicular to a surface of the housing, the conductive segment of the loading portion configured to adjust the input impedance of the implantable telemetry antenna by reducing or about canceling a capacitive portion of the input impedance of the implantable telemetry antenna.

In Example 17, the subject matter of one or any combination of Examples 11-16 can optionally include a dielectric compartment of the implantable medical device comprising a header configured to provide an electrical and mechanical connection to an implantable lead, the implantable lead including an electrode configured for location at a tissue site, and coupled to electronic circuitry within the housing to provide one or more of electrostimulation of tissue, or sensing of activity, at the site of the electrode.

In Example 18, the subject matter of one or any combination of Examples 11-17 can optionally include an implantable lead and the electrode.

In Example 19, the subject matter of one or any combination of Examples 11-18 can optionally include a portion of the spiral conductor located toward the housing and is oriented so that the sidewall provides a face located near the housing that is substantially parallel to a surface of the housing.

Example 20 can include, or can optionally be combined with the subject matter of one or any combination of Examples 1-19 to include, subject matter (such as a method, a means for performing acts, or a machine-readable medium including instructions that, when performed by the machine, cause the machine to perform acts) comprising providing an implantable medical device, including a dielectric compartment including first and second substantially parallel face portions, and a third face portion extending between the first and second face portions, an implantable telemetry antenna, located at least partially within the dielectric compartment, the implantable telemetry antenna comprising a spiral conductor portion extending along the first, second, and third face portions, and wirelessly transferring information electromagnetically using the implantable telemetry antenna.

Example 21 includes subject matter (such as an apparatus) comprising an implantable medical device including a housing, an implantable telemetry circuit carried within the housing, a dielectric compartment, mechanically coupled to the housing, an implantable telemetry antenna, located at least partially within the dielectric compartment, the implantable telemetry circuit electrically coupled to the implantable telemetry antenna and configured to wirelessly transfer information electromagnetically using the implantable telemetry antenna. In Example 21, the implantable telemetry antenna comprises a spiral conductor portion extending along a face portion of the dielectric compartment, a loading portion, coupled to the spiral conductor portion and the implantable telemetry circuit, the loading portion comprising a conductive segment substantially perpendicular to a surface of the housing, the conductive segment of the loading portion configured to adjust an input impedance of the implantable telemetry antenna, to provide a specified input impedance range within a specified range of operating frequencies to be used for wireless information transfer.

In Example 22, the subject matter of Example 21 can optionally include a spiral conductor including a planar spiral pattern including concentric turns, the planar spiral pattern folded so that a portion of the planar spiral pattern is located near, and substantially parallel to, the face portion of the dielectric compartment.

In Example 23, the subject matter of one or any combination of Examples 21-22 can optionally include a dielectric compartment includes first and second substantially parallel face portions, and a third face portion extending between the first and second face portions, the implantable telemetry antenna including a spiral conductor portion extending along the first, second, and third face portions.

In Example 24, the subject matter of one or any combination of Examples 21-23 can optionally include a loading portion configured to adjust the input impedance of the implantable telemetry antenna by adjusting or about canceling a capacitive portion of the input impedance of the implantable telemetry antenna.

In Example 25, the subject matter of one or any combination of Examples 21-24 can optionally include a dielectric compartment of the implantable medical device comprising a header configured to provide an electrical and mechanical connection to an implantable lead, the implantable lead including an electrode configured for location at a tissue site, and coupled to electronic circuitry within the housing to provide one or more of electrostimulation of tissue, or sensing of activity, at the site of the electrode.

In Example 26, the subject matter of one or any combination of Examples 21-25 can optionally include an implantable lead and the electrode.

In Example 27, the subject matter of one or any combination of Examples 21-26 can optionally include a spiral conductor including a cross section having a lateral width that is greater than a sidewall height of the cross section.

In Example 28, the subject matter of one or any combination of Examples 21-27 can optionally include a portion of the spiral conductor located toward the housing and is oriented so that the sidewall provides a face located near the housing that is substantially parallel to a surface of the housing.

In Example 29, the subject matter of one or any combination of Examples 21-28 can optionally include a separation between adjacent turns of the spiral conductor decreased as compared to using a cross section lacking the lateral width greater than the sidewall height to provide the specified input impedance range within the specified range of operating frequencies.

In Example 30, the subject matter of one or any combination of Examples 21-29 can optionally include a total surface area of the implantable telemetry antenna increased as compared to using a cross section lacking the lateral width greater than the sidewall height to provide the specified input impedance range within the specified range of operating frequencies.

In Example 31, the subject matter of one or any combination of Examples 21-30 can optionally include one or more of a number of turns of the spiral conductor, the lateral width of the spiral conductor, the sidewall height of the spiral conductor, a separation between adjacent turns of the spiral conductor, a path length along the spiral conductor, a total surface area of the antenna, a diameter of a hypothetical sphere sized to enclose the antenna, or a separation between an end and an initial location along the antenna, is used to provide the specified input impedance range, within a specified range of operating frequencies to be used for wireless information transfer.

In Example 32, the subject matter of one or any combination of Examples 21-31 can optionally include a spiral conductor portion defining a hypothetical axis around which the spiral winds, the conductive spiral portion including a first winding that is offset in depth along the hypothetical axis from a second winding of the conductive spiral, and the hypothetical axis substantially perpendicular to the face portion of the dielectric compartment, and a total depth of the spiral antenna, along the hypothetical axis, is at least an order of magnitude smaller than a diameter or a largest linear dimension of a surface area enclosed by an outer-most turn of the spiral conductor.

In Example 33, the subject matter of one or any combination of Examples 21-32 can optionally include a spiral conductor including one or more of a tapered cross-sectional lateral width or a tapered spacing between adjacent turns, along the spiral conductor.

Example 34 includes subject matter (such as an apparatus) comprising an implantable medical device, including a housing, an implantable telemetry circuit carried within the housing, a dielectric compartment, mechanically coupled to the housing, an implantable telemetry antenna, located at least partially within the dielectric compartment, the implantable telemetry circuit electrically coupled to the implantable telemetry antenna and configured to wirelessly transfer information electromagnetically using the implantable telemetry antenna, the implantable telemetry antenna including a spiral conductor portion extending along a face portion of the dielectric compartment, the spiral conductor including one or more of a tapered cross-sectional lateral width or a tapered spacing between adjacent turns, along the spiral conductor, a loading portion, coupled to the spiral conductor portion and the implantable telemetry circuit, the loading portion comprising a conductive segment substantially perpendicular to a surface of the housing, the conductive segment of the loading portion configured to adjust an input impedance of the implantable telemetry antenna, to provide a specified input impedance range within a specified range of operating frequencies to be used for wireless information transfer.

Example 35 can include, or can optionally be combined with the subject matter of one or any combination of Examples 1-34 to include, subject matter (such as a method, a means for performing acts, or a machine-readable medium including instructions that, when performed by the machine, cause the machine to perform acts) comprising providing an implantable medical device including a dielectric compartment including first and second substantially parallel face portions, a third face portion extending between the first and second face portions, and an implantable telemetry antenna, located at least partially within the dielectric compartment, the implantable telemetry antenna comprising a spiral conductor portion extending along a face portion of the dielectric compartment and a loading portion, coupled to the spiral conductor portion and the implantable telemetry circuit, the loading portion comprising a conductive segment substantially perpendicular to a surface of the housing, the conductive segment of the loading portion configured to adjust an input impedance of the implantable telemetry antenna, to provide a specified input impedance range within a specified range of operating frequencies to be used for wireless information transfer, and wirelessly transferring information electromagnetically using the implantable telemetry antenna.

In Example 36, the subject matter of Example 35 can optionally include a spiral conductor comprising a planar spiral pattern including concentric turns, the planar spiral pattern folded so that a portion of the planar spiral pattern is located near, and substantially parallel to, the face portion of the dielectric compartment.

In Example 37, the subject matter of one or any combination of Examples 35-36 can optionally include a dielectric compartment comprising first and second substantially parallel face portions, and a third face portion extending between the first and second face portions, and the implantable telemetry antenna comprising a spiral conductor portion extending along the first, second, and third face portions.

In Example 38, the subject matter of one or any combination of Examples 35-37 can optionally include adjusting the input impedance of the implantable telemetry antenna by adjusting or about canceling a capacitive portion of the input impedance of the implantable telemetry antenna.

In Example 39, the subject matter of one or any combination of Examples 35-38 can optionally include a spiral conductor comprising a cross section having a lateral width that is greater than a sidewall height of the cross section, and adjusting the input impedance of the implantable telemetry antenna using one or more of a number of turns of the spiral conductor, the lateral width of the spiral conductor, the sidewall height of the spiral conductor, a separation between adjacent turns of the spiral conductor, a path length along the spiral conductor, a total surface area of the antenna, a diameter of a hypothetical sphere sized to enclose the antenna, or a separation between an end and an initial location along the antenna, to provide a specified input impedance range, within a specified range of operating frequencies to be used for wireless information transfer.

In Example 40, the subject matter of one or any combination of Examples 35-39 can optionally include a spiral conductor comprising one or more of a tapered cross-sectional lateral width or a tapered spacing between adjacent turns, along the spiral conductor.

Example 41 includes subject matter (such as an apparatus) comprising an implantable antenna assembly, including a dielectric shell including first and second substantially parallel outer face portions, and a third outer face portion extending between the first and second portions, a spiral conductor extending along the first, second, and third portions on a surface of the dielectric shell, the dielectric shell and spiral conductor configured to be mechanically attached to a dielectric compartment configured to be coupled to a housing of an implantable medical device, the implantable antenna assembly configured to be electrically coupled to an implantable telemetry circuit configured to wirelessly transfer information electromagnetically using the implantable telemetry antenna.

In Example 42, the subject matter of Example 41 can optionally include a spiral conductor configured to extend along an interior-facing surface of the dielectric shell.

In Example 43, the subject matter of one or any combination of Examples 41-42 can optionally include a spiral conductor configured to extend along an exterior-facing surface of the dielectric shell.

In Example 44, the subject matter of one or any combination of Examples 41-43 can optionally include a dielectric shell and spiral conductor configured to be contained at least partially within the dielectric compartment by a material comprising at least a portion of the dielectric compartment.

In Example 45, the subject matter of one or any combination of Examples 41-44 can optionally include a dielectric shell configured to mechanically retain the spiral conductor, using at least one of a stake or a channel.

In Example 46, the subject matter of one or any combination of Examples 41-45 can optionally include a stake configured to retain a portion of the spiral conductor when the stake is deformed.

In Example 47, the subject matter of one or any combination of Examples 41-46 can optionally include a dielectric shell configured to mechanically immobilize the spiral conductor when the dielectric shell is molded around at least a portion of the spiral conductor.

In Example 48, the subject matter of one or any combination of Examples 41-47 can optionally include one or more of the dielectric shell or the spiral conductor adhesively attached to the dielectric compartment.

In Example 49, the subject matter of one or any combination of Examples 41-48 can optionally include an implantable medical device including the housing, the dielectric compartment, mechanically coupled to the housing and mechanically coupled to the implantable antenna assembly, the implantable telemetry circuit carried within the housing and configured to wirelessly transfer information electromagnetically using the implantable antenna assembly.

In Example 50, the subject matter of one or any combination of Examples 41-49 can optionally include a dielectric compartment of the implantable medical device comprising a header configured to provide an electrical and mechanical connection to an implantable lead, the implantable lead including an electrode configured for location at a tissue site, and coupled to electronic circuitry within the housing to provide one or more of electrostimulation of tissue, or sensing of activity, at the site of the electrode.

In Example 51, the subject matter of one or any combination of Examples 41-50 can optionally include an implantable lead and the electrode.

Example 52 includes subject matter (such as an apparatus) comprising an implantable antenna assembly, comprising a dielectric core including first and second substantially parallel face portions, and a third face portion extending between the first and second portions, a cavity sized and shaped to accept an implantable lead connector, a spiral conductor extending along the first, second, and third portions on an exterior surface of the dielectric core, the dielectric core and spiral conductor are configured to be at least partially contained within a dielectric compartment, and the implantable antenna assembly configured to be electrically coupled to an implantable telemetry circuit configured to wirelessly transfer information electromagnetically using the implantable telemetry antenna.

In Example 53, the subject matter of Example 52 can optionally include a dielectric core configured to mechanically retain the spiral conductor, using at least one of a stake or a channel.

In Example 54, the subject matter of one or any combination of Examples 52-53 can optionally include a dielectric core configured to mechanically immobilize the spiral conductor when the dielectric core is molded around at least a portion of the spiral conductor.

In Example 55, the subject matter of one or any combination of Examples 52-54 can optionally include an implantable medical device including the housing, the dielectric compartment, mechanically coupled to the housing and mechanically coupled to the implantable antenna assembly, and the implantable telemetry circuit carried within the housing and configured to wirelessly transfer information electromagnetically using the implantable antenna assembly.

In Example 56, the subject matter of one or any combination of Examples 52-55 can optionally include a combination of the dielectric compartment and the dielectric core comprising a header configured to provide an electrical and mechanical connection to an implantable lead, the implantable lead including an electrode configured for location at a tissue site and coupled to electronic circuitry within the housing to provide one or more of electrostimulation of tissue, or sensing of activity, at the site of the electrode.

In Example 57, the subject matter of one or any combination of Examples 52-56 can optionally include an implantable lead and the electrode.

Example 58 can include, or can optionally be combined with the subject matter of one or any combination of Examples 1-57 to include, subject matter (such as a method, a means for performing acts, or a machine-readable medium including instructions that, when performed by the machine, cause the machine to perform acts) comprising attaching a spiral conductor to a dielectric shell, the dielectric shell including first and second substantially parallel outer face portions, and a third outer face portion extending between the first and second portions, the spiral conductor configured to extend along the first, second, and third portions on a surface of the dielectric shell, and mechanically coupling the dielectric shell and the spiral conductor to a dielectric compartment configured to be coupled to a housing of an implantable medical device.

In Example 59, the subject matter of Example 58 can optionally include mechanically coupling the dielectric shell and spiral conductor to the dielectric compartment including overmolding the dielectric shell and spiral conductor using a material comprising at least a portion of the dielectric compartment.

In Example 60, the subject matter of one or any combination of Examples 58-59 can optionally include mechanically coupling the dielectric shell and spiral conductor to the dielectric compartment including adhesively coupling the dielectric shell or the spiral conductor to the dielectric compartment.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:
1. An apparatus, comprising:
an implantable medical device comprising:
a housing;
an implantable telemetry circuit carried within the housing;

a dielectric compartment, mechanically coupled to the housing, the dielectric compartment including first and second substantially parallel face portions, and a third face portion extending between the first and second face portions;

an implantable telemetry antenna, located at least partially within the dielectric compartment;

wherein the implantable telemetry circuit is electrically coupled to the implantable telemetry antenna and configured to wirelessly transfer information electromagnetically using the implantable telemetry antenna; and wherein the implantable telemetry antenna comprises:
a spiral conductor extending along and substantially conforming to the contours of the first, second, and third face portions of the dielectric compartment, wherein the spiral conductor comprises a planar spiral pattern including concentric turns; and a loading portion, coupled to the spiral conductor and the implantable telemetry circuit, the loading portion comprising a conductive segment substantially perpendicular to a surface of the housing, the conductive segment of the loading portion configured to adjust an input impedance of the implantable telemetry antenna, to provide a specified input impedance range within a specified range of operating frequencies to be used for wireless information transfer.

2. The apparatus of claim 1, wherein the planar spiral pattern is folded so that a portion of the planar spiral pattern is located near, and substantially parallel to, the third face portion of the dielectric compartment.

3. The apparatus of claim 1, wherein the loading portion is configured to adjust the input impedance of the implantable telemetry antenna by adjusting or about canceling a capacitive portion of the input impedance of the implantable telemetry antenna.

4. The apparatus of claim 1, wherein the dielectric compartment of the implantable medical device comprises a header configured to provide an electrical and mechanical connection to an implantable lead, the implantable lead including an electrode configured for location at a tissue site, and coupled to electronic circuitry within the housing to provide one or more of electrostimulation of tissue, or sensing of activity, at the site of the electrode.

5. The apparatus of claim 4, further comprising the implantable lead and the electrode.

6. The apparatus of claim 1, wherein the spiral conductor includes a cross section having a lateral width that is greater than a sidewall height of the cross section.

7. The apparatus of claim 6, wherein a portion of the spiral conductor is located toward the housing and is oriented so that the sidewall provides a face located near the housing that is substantially parallel to a surface of the housing.

8. The apparatus of claim 6, wherein the separation between adjacent turns of the spiral conductor is decreased as compared to using a cross section lacking the lateral width greater than the sidewall height to provide the specified input impedance range within the specified range of operating frequencies.

9. The apparatus of claim 6, wherein the total surface area of the implantable telemetry antenna is increased as compared to using a cross section lacking the lateral width greater than the sidewall height to provide the specified input impedance range within the specified range of operating frequencies.

10. The apparatus of claim 6, wherein one or more of a number of turns of the spiral conductor, the lateral width of the spiral conductor, the sidewall height of the spiral conductor, a separation between adjacent turns of the spiral conductor, a path length along the spiral conductor, a total surface area of the antenna, a diameter of a hypothetical sphere sized to enclose the antenna, or a separation between an end and an initial location along the antenna, is used to provide the specified input impedance range, within a specified range of operating frequencies to be used for wireless information transfer.

11. The apparatus of claim 1, wherein the spiral conductor portion defines a hypothetical axis around which the spiral winds, the conductive spiral portion including a first winding that is offset in depth along the hypothetical axis from a second winding of the conductive spiral, and the hypothetical axis substantially perpendicular to the face portion of the dielectric compartment; and wherein a total depth of the spiral antenna, along the hypothetical axis, is at least an order of magnitude smaller than a diameter or a largest linear dimension of a surface area enclosed by an outer-most turn of the spiral conductor.

12. The apparatus of claim 1, wherein the spiral conductor includes one or more of a tapered cross-sectional lateral width or a tapered spacing between adjacent turns, along the spiral conductor.

13. An apparatus, comprising:
an implantable medical device comprising:
a housing;
a dielectric compartment, mechanically coupled to the housing, the dielectric compartment including first and second substantially parallel face portions, and a third face portion extending between the first and second face portions;

an implantable telemetry circuit carried within the housing;

an implantable telemetry antenna, located at least partially within the dielectric compartment;

wherein the implantable telemetry circuit is electrically coupled to the implantable telemetry antenna and configured to wirelessly transfer information electromagnetically using the implantable telemetry antenna; and wherein the implantable telemetry antenna comprises:
a spiral conductor extending along and substantially conforming to the contours of the first, second, and third face portions of the dielectric compartment, the spiral conductor including one or more of a tapered cross-sectional lateral width or a tapered spacing between adjacent turns, along the spiral conductor, wherein the spiral conductor comprises a planar spiral pattern including concentric turns; and a loading portion, coupled to the spiral conductor portion and the implantable telemetry circuit, the loading portion comprising a conductive segment substantially perpendicular to a surface of the housing, the conductive segment of the loading portion configured to adjust an input impedance of the implantable telemetry antenna, to provide a specified input impedance range within a specified range of operating frequencies to be used for wireless information transfer.

14. A method, comprising:
providing an implantable medical device comprising:
- a dielectric compartment including first and second substantially parallel face portions, and a third face portion extending between the first and second face portions; and
- an implantable telemetry antenna, located at least partially within the dielectric compartment, the implantable telemetry antenna comprising:
    - a spiral conductor portion extending along and substantially conforming to the contours of the first, second, and third face portions of the dielectric compartment, wherein the spiral conductor comprises a planar spiral pattern including concentric turns; and
    - a loading portion, coupled to the spiral conductor portion and the implantable telemetry circuit, the loading portion comprising a conductive segment substantially perpendicular to a surface of the housing, the conductive segment of the loading portion configured to adjust an input impedance of the implantable telemetry antenna, to provide a specified input impedance range within a specified range of operating frequencies to be used for wireless information transfer; and wirelessly transferring information electromagnetically using the implantable telemetry antenna.

15. The method of claim 14, wherein the planar spiral pattern is folded so that a portion of the planar spiral pattern is located near, and substantially parallel to, the third face portion of the dielectric compartment.

16. The method of claim 14, comprising adjusting the input impedance of the implantable telemetry antenna by adjusting or about canceling a capacitive portion of the input impedance of the implantable telemetry antenna.

17. The method of claim 14, wherein the spiral conductor includes a cross section having a lateral width that is greater than a sidewall height of the cross section; and wherein the method comprises adjusting the input impedance of the implantable telemetry antenna using one or more of a number of turns of the spiral conductor, the lateral width of the spiral conductor, the sidewall height of the spiral conductor, a separation between adjacent turns of the spiral conductor, a path length along the spiral conductor, a total surface area of the antenna, a diameter of a hypothetical sphere sized to enclose the antenna, or a separation between an end and an initial location along the antenna, to provide a specified input impedance range, within a specified range of operating frequencies to be used for wireless information transfer.

18. The method of claim 14, wherein the spiral conductor includes one or more of a tapered cross-sectional lateral width or a tapered spacing between adjacent turns, along the spiral conductor.

* * * * *